United States Patent [19]
Dunn et al.

[11] Patent Number: 5,643,763
[45] Date of Patent: Jul. 1, 1997

[54] METHOD FOR MAKING RECOMBINANT YEAST ARTIFICIAL CHROMOSOMES BY MINIMIZING DIPLOID DOUBLING DURING MATING

[75] Inventors: Barbara Dunn, Los Altos; Theodore K. Choi, Berkeley, both of Calif.

[73] Assignee: Genpharm International, Inc., Mountain View, Calif.

[21] Appl. No.: 335,116

[22] Filed: Nov. 4, 1994

[51] Int. Cl.⁶ .............................. C12P 19/34; C12Q 1/68; C12N 15/70; C07H 21/04
[52] U.S. Cl. .............. 435/91.1; 435/6; 435/91.2; 435/320.1; 536/24.3; 536/24.31; 536/24.32; 536/24.33
[58] Field of Search .............. 435/6, 91.1, 91.2, 435/320.1; 536/24.3, 24.31, 24.32, 24.33

[56] References Cited

U.S. PATENT DOCUMENTS 4,889,806  12/1989  Olson et al. ................... 435/172.3

FOREIGN PATENT DOCUMENTS

WO92/01069  1/1992  WIPO.
WO95/03400  2/1995  WIPO.

OTHER PUBLICATIONS

Sena et al, "Synchronous mating in Yeast", Proc. Natl. Acad. Sci. 70(5):1373–1377 May 1973.
Higuchi et al, "Recombinant PCR" in PCR Protocols:A Guide to Methods and Applications, Academic Press, San Diego, California, pp. 177–183 1990.
Ketner et al, "Efficient manipulation of the human adenovirus genome as an infectious yeast artificial chromosome clone", Proc. Natl. Acad. Sci. 91:6186–6190 Jun. 1994.
Rotomondo et al, "Genetic selection of meiotic and mitotic recombinant yeast artificial chromosomes", Nucleic Acids Res. 22(7):1208–1214 Apr. 1994.

Den Dunnen et al, "YAC Breeding to reconsitute large loci", in YAC libraries: A User's Guide, W.H. Freeman and Co., New York, pp. 182–202 Aug. 1993.
Spencer et al, "Targeted recombination based cloning and manipulation of large DNA segments in Yeast", Methods 5:161–175 Aug. 1993.
Cloning of Large Segments of Exogenous DNA into Yeast by Means of Artificial Chromosome Vectors, Burke et al., Science, vol. 236, pp. 806–812, May 15, 1987.
Preparation of Clone Libraries in Yeast Artificial–Chromosome Vectors, Burke et al. Methods in Enzymology, vol. 194, pp. 251–270, 1991.
Mapping the Whole Genome by Fingerprinting Yeast Artificial Chromosomes, Bellanne–Chantelot, et al., Cell, vol. 70, pp. 1059–1068 (1992).
Detection of Homolgous Recombination Between Yeast Artificial Chromosomes with Overlapping Inserts, Cellini, et al., Nucleic Acids Research, vol. 19:5, pp. 997–1000 (1991).

(List continued on next page.)

*Primary Examiner*—George C. Elliott
*Assistant Examiner*—Jeffrey Fredman
*Attorney, Agent, or Firm*—Cooley Godward LLP

[57] ABSTRACT

The present invention provides methods for construction of recombinant Yeast Artificial Chromosomes ("YAC") by homologous recombination between YACs during meiosis. In particular, conditions are provided for the step of mating haploid cells and for the step of spore analysis that increase the frequency of spores containing the desired recombinant YAC. The methods find particular use in constructing recombinant YACs between YACs that are incompatible when co-propagated in a diploid and/or that share homology regions of less than about 50 kilobases. Linking YACs, methods of their construction, and methods of their use are provided that allow facile construction of a YAC containing two or more discontinuous regions of DNA.

22 Claims, 9 Drawing Sheets

OTHER PUBLICATIONS

Chromosomal Region of the Cystic Fibrosis Gene in Yeast Artificial Chromosomes: A Model for Human Genome Mapping, Green et al., Science, vol. 250, pp. 94–98 (1990).

Meiotic Recombination and Segregation of Human–Derived Artificial Chromosomes in Saccharmyces Cerevisiae, Sears, et al., Proc. Natl. Acad. Sci., vol. 89, p. 5296–5300 (1992).

Reconstruction of the 2.4 Mb Human DMD–gene by Homologous YAC Recombination, Dunhen, et al., Human Molecular Genetics, vol. 1:1, pp. 19–28 (1992).

METHOD FOR MAKING RECOMBINANT YEAST ARTIFICIAL CHROMOSOMES BY MINIMIZING DIPLOID DOUBLING DURING MATING

ACKNOWLEDGEMENTS

This invention was supported in part by grants from ATP grant number NIST CRADA 70NANB3H1366 and from NIH SBIR grant number NIAID AI32285-03. The U.S. Government may have rights in this invention.

INTRODUCTION

1. Technical Field

This invention relates to methods of construction of Yeast Artificial Chromosomes ("YACS") by homologous recombination.

2. Background

Yeast Artificial Chromosome ("YAC") cloning vectors are capable of propagating large (50 to more than 1000 kilobases) cloned inserts (U.S. Pat. No. 4,889,806) of xenogenic DNA. To date, an upper limit for insert size has not been determined. YAC clone libraries have been used to identify, map, and propagate large fragments of mammalian genomic DNA. YAC cloning is especially useful for isolating intact genes, particularly large genes having exons distributed over several tens of kilobases or more, and genes having distal regulatory elements located tens of kilobases or more upstream or downstream from the exonic sequences. YAC cloning is particularly advantageous for isolating large complex gene loci, such as unrearranged immunoglobulin gene loci. YAC cloning is also well-suited for making vectors for performing targeted homologous recombination in mammalian cells, since YACs allow the cloning of large contiguous sequences useful as recombinogenic homology regions in homologous targeting vectors. Moreover, YACs afford a system for doing targeted homologous recombination in a yeast host cell to create novel, large transgenes (e.g., large minigenes, tandem gene arrays, etc.) in YAC constructs which could then be transferred to mammalian host cells.

Unfortunately, manipulation of large polynucleotides is problematic. Large polynucleotides are susceptible to breakage by shearing forces and form highly viscous solutions even at relatively dilute concentrations, making in vitro manipulation exceedingly difficult. For these reasons, and others, it is desirable to reduce the amount of in vitro manipulation that YAC clones and other large DNA fragments are subjected to in the process of constructing large transgene constructs or homologous recombination constructs.

Cloning of large fragments of genomic DNA in YACs has become a general approach to study the physical organization of complex genomes (Burke, et al. (1987) Science 236:806:812). The average insert size of currently available YAC libraries varies between 250 kb (Burke and Olson (1991) Methods Enymol. 194:251–270) and more recently 850 kb (Bellane-Chantelot et al. (1992) Cell 70:1059–1068). Some genes (CFTR, BCL2, DMD), or their regulatory elements, extend over several hundreds of kilobases, and therefore, are not always going to be present within a single YAC. Moreover, the detailed analysis of several YAC libraries has revealed a high percentage (up to 50%) of chimeric clones (Green and Olson (1990) Nature 250:94–98), implying that even positive clones carrying large inserts, might be of limited usage.

Recently, meiotic homologous recombination in yeast has been used to reconstruct larger yeast artificial chromosomes starting from a diploid yeast carrying two overlapping YACs. Using this approach, Green and Olson (Ibid.) were able to build recombinant YACs up to 790 kb, thereby containing about half the DNA isolated from the cystic fibrosis gene region on human chromosome 7. Since the parental YACs were carrying identical pairs of selectable markers (TRP1 and URA3), the recombinant clones were identified by using screening by physical assays (e.g. PCR-based assessment of previously defined sequenced-tagged sites ("STS") content, and size measurements by pulsed-field gel electrophoresis). Prior to recombining, YACs were analyzed for common regions, i.e. overlaps, and diploids containing a pair of YACs with appropriately overlapping (i.e. sharing long regions of homology oriented in the same direction with respect to the YAC arms) regions for meiotic recombination were constructed. One recombinant YAC, pCF-1/7-R, of about 600 kb was constructed by recombination of two YACs reportedly having an overlap of 40–50 kb of homology by screening 76 spores. Cellini et al. (Nuceleic Acids Research (1991) 997–1000) reported a YAC vector (PYACR) with LEU2 as an auxotrophic marker on the right arm, but with no markers on the left arm. The genetic selection reported by Cellini et al. for one of the recombinant YACs is presently of limited usage due to the lack of available YAC libraries constructed in a leu2⁻ host. None of the above methods reported successful recombination of YACs sharing less than about 40–50 kb of homology nor of pairs of YACs that were observed to be mitotically incompatible during attempts to propagate them in the same diploid.

Sears et al. (1992 PNAS USA 89:5296–5300) developed a YAC based recombination system to study factors contributing to the fidelity of meiotic chromosome transmission. They were able to show that the relationship between physical distance and recombination frequency within the human DNA segment insert was comparable that of endogenous yeast chromosomal DNA (2.0 to 7.7 kb/cM). They used meiotic recombination between YACs presenting 50–360 kb of overlap. Only diploids containing pairs of YACS that were mitotically compatible were used.

Den Dunnen et al. (1992 Human Molecular Genetics 1:19–28) also took advantage of homologous recombination to reconstruct the majority of the human DMD gene in a single recombinant YAC of 2.3 Mb. They used meiotic recombination between YACs presenting 150–460 kb of overlap and that were mitotically compatible in the diploid. However, Den Dunnen observed that some pairs of YACs did not lead to isolation of desired recombinants because mitotic propagation of the YAC pair in the diploid, prior to meiosis, resulted in the loss and/or gross rearrangement (observed as a change in size) of one or both YACs; this behavior was referred to as diploid incompatibility. Recombination was not obtained with YACs that were found to be mitotically incompatible when attempts were made to co-propagate them in a diploid.

Currently the introduction of multiple and disperse genes into a target cell or animal necessitates separate transfection/integration steps for each gene typically followed by tedious screening and breeding procedures to derive a transgenic cell or animal having each of the separate genes. Coinjection of the multiple and disperse genes is problematic in part because a resulting transgene array (assuming one would achieve genetically linked cointegration) would be unpredictable and uncontrollable, such that the stoichiometry of the component genes of the transgene array could not be controlled, and structural analysis of the transgene array would be very difficult if not impossible to achieve.

Thus, there exists a need in the art for an efficient and versatile method of preparing large segments of DNA in YAC clones with a minimum of time, manipulation, and cloning procedures. In particular, it would be highly advantageous if it were possible to obtain cloned mammalian genomic fragment from a YAC library by recombination of YACs without additional cloning or manipulation (e.g., ligation of the sequences to each other), with minimal screening to find appropriately overlapping YACs, and without the need to pre-screen for, or be reliant upon, diploid compatibility of YAC pairs. Such a recombinant process would be useful to construct larger yeast artificial chromosomes from smaller overlapping ones, to eliminate the chimeric parts of some YACs, to reconstruct a clone containing a large genomic region of interest, and as a means to construct large DNAs of a desired design, for example, one that would combine genomic regions naturally separated by undesirable or unclonable regions or one that would create clusters of genes that are not normally grouped.

SUMMARY OF THE INVENTION

It is an object of the present invention to provide methods for constructing large DNA constructs as Yeast Artificial Chromosomes by homologous recombination between YACs (referred to as parental or input YACs) during meiosis in yeast. In general, homologous recombination between a pair of YACs that share a region of homology is obtained from a process that includes a mating step, a sporulation step and an identification step. In brief, the process includes the steps of (1) first mating yeast cells of opposite mating types, where each type contains one YAC of the YAC pair to be recombined, to form a diploid that contains both input YACs, then (2) sporulating the diploid, i.e. inducing the diploid to undergo meiotic division and haploid spore formation, usually by nitrogen starvation, during which recombination between the YAC pair can occur, and (3) subsequently identifying (and isolating) those haploid spores bearing a desired recombinant YAC. Although the invention can be applied to recombination between any YAC pair sharing relatively large regions of homology or between a YAC pair displaying mitotic stability when co-propagated in a diploid, the methods of the invention find particular use when applied to YACs with homology regions of less than about 50 kb, preferably less than about 40 kb, and/or, most preferably, that display mitotic incompatibility when attempts are made to co-propagate them in a diploid. Accordingly, it is an object of the invention to provide methods that increase the frequency of haploid yeast spores containing the desired recombinant YAC after the sporulation step, and to provide methods that select preferentially for desired haploid cells containing the desired recombinant YAC from the spore population to thus increase the frequency of desired cells in the population of cells to be analyzed for the presence of the desired recombinant YAC. According to the invention, methods, which include steps for construction and manipulation of diploids prior to sporulation and steps for subsequent genetic selection of YAC-containing spores, which steps can be used separately or, most preferably, in combination to best achieve the foregoing objects.

According to the invention methods for diploid construction are provided such that during the mating step a diploid yeast cell, containing a pair of parent (or input) YACs that share a homology region suitable to enable homologous recombination between them during meiosis, will maintain both input YACs without rearrangement upon entering the sporulation step. This is accomplished by minimizing or preventing diploid growth, i.e. mitotic division (doubling) of the diploid cell, immediately after mating during the mating step. Diploid growth during mating is limited to about 8 or fewer diploid doublings or most preferably prevented. When mass matings, i.e. mixing of cultures of the parental haploid yeast cells, are performed, mitotic growth is most preferably prevented or is limited by limiting the mating period to a period of time equal to or less than 8 diploid-doubling times. Preferably mating is performed in the absence of selection for markers located on the YAC arms. Recombination (meiotic recombination) is induced by sporulating the diploid or diploids. The resulting cell mixture, containing spores, diploids, and unmated parented haploids, is then enriched for (haploid) spores. The spores can be screened by the usual methods in the art for the desired recombinant YAC, or preferably, a method of genetic selection according to the invention, as presented below, is followed in order to select for and enhance identification of spores containing the desired YAC.

Methods are provided for the spore analysis step that facilitate detection and identification of spores having the desired recombinant YAC by performing a genetic selection for yeast spores containing the desired recombinant YAC, while optionally counter-selecting (i.e. selecting against) for parental YACs or the undesired by-product recombinant YAC. According to the invention, genetic selection is designed by providing the input YACs with selectable markers such that YAC recombination results in the desired recombinant YAC predictably having a certain selectable marker, or preferably markers, that allow application of a genetic selection for the marker or markers to allow growth of spores containing the desired recombinant YAC and optionally to select against the marker or markers present on the undesired byproduct recombinant YAC, or further optionally select against cells with parental YACs. After diploid construction, preferably by a method of diploid construction according to the present invention, and sporulation, spores are enriched with respect to diploids and unmated parent haploids by methods known in the art, and the enriched spore population is subjected to genetic selection in media that selects for the desired recombinant YAC and, optionally but preferably, counter-selects for the undesired by-product recombinant YAC and further optionally but most preferably counter selects for parental YACs, (e.g., spores with unrecombined parental YACs residual parental diploids). As a consequence of the method of the invention, the resulting surviving cell population has an increased frequency of haploid cells containing the desired YAC, and accordingly, the subsequent screening and analysis for cells harboring the desired recombinant YAC is greatly simplified and expedited.

Although either the step of minimization of diploid mitotic growth or the step of genetic selection, preferably selection for the desired recombinant YAC and against undesired YACs, can be performed without the other as a step in a known YAC recombination protocol, in the most preferred embodiment of the invention both steps are performed.

The invention finds particular use in constructing large DNA constructs of transgenes and large homologous targeting constructs spanning at least one complete transcriptional complex, suitable for transfer into mammalian cells, such as embryonic stem ("ES") cells, typically for construction of a transgenic animal. The methods of the present invention also find particular use in constructing minigenes that comprise clusters of genes that are not normally found clustered in a genome or that are located in different genomes.

Furthermore, the invention, particular linking YACs and their methods of use, finds use not only in adjoining large regions of discontinuous DNA, but also in engineering large DNA constructs by adjoining DNA constructs such that undesirable regions in the starting materials are excluded from the final recombinant product.

Finally, novel methods of making the linking YACs of the invention are provided that minimize steps involving DNA isolation and host cell transformation.

BRIEF DESCRIPTION OF THE DRAWINGS

FIG. 9A shows the isolation of YAC endclone fragments by LR-PCR. The four primers for LR-PCR of endclone inserts (S3CX, S2CR1, S2' AX1, and S1AR) are depicted as shaded rectangles. S3CX and S1AR contain NotI sites. S2CR1 and S2' AX1 contain i-SCEI sites. FIG. 9B shows the cutting of LR-PCR products with i-SCEI. Digestion of LR-PCR products with i-SCEI, ligation, and digestion with NotI yields three predominant dimer molecules, the desired heterodimer (denoted (a)), the 10.33 homodimer (denoted (b)), and the J1XK.31 homodimer (denoted (c)). Product (a) is isolated from (b) and (c) by size fractionation by preparative pulsed field gel electrophoresis. Primer sequences are provided in Example 11.

DESCRIPTION OF SPECIFIC EMBODIMENTS

Figure 1:
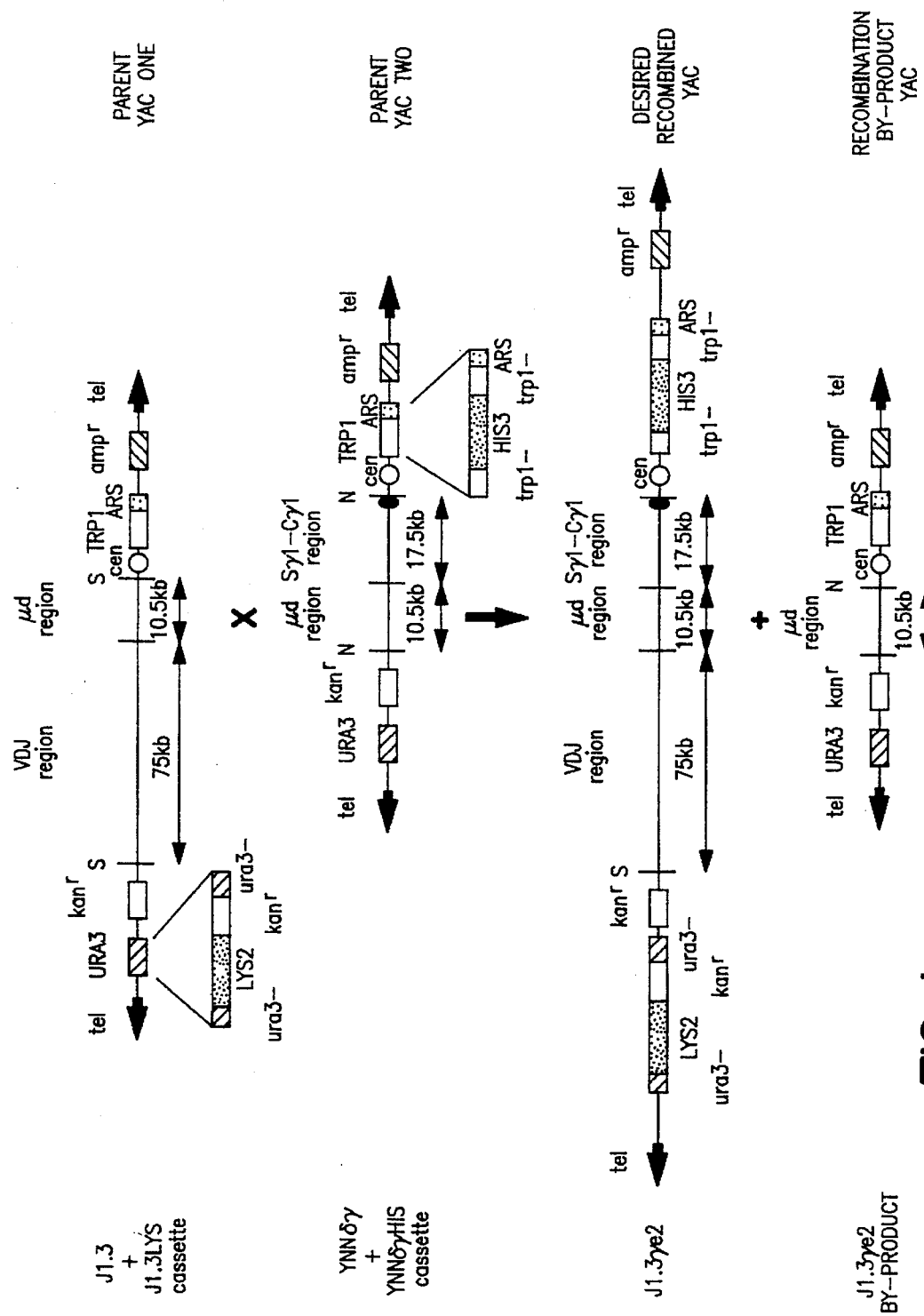
FIG. 1 is a schematic depicting recombination between YAC pairs J1.3LYS and YNN-δγ-HIS to produce J1.3γe2. The YAC vector arms are essentially as described in "YAC Libraries, a users guide", Nelson and Brownstein, eds. All the YACs carry telomeric elements (denoted by heavy arrowheads) at the ends of the YAC. The URA3, TRP1, HIS3 and LYS2 yeast selectable marker cassettes are denoted as striped, open, dark, and dark boxes respectively. The ARS cassette adjacent to the TRP1 cassette is depicted as a grey box. The open circle marked "cen" denotes the yeast centromere, while the striped and filled boxes marked "amp$^r$" and "kan$^r$" denote the bacterial ampicillin resistance gene and the kanamycin resistance gene respectively. Replacement of the URA3 marker on J1.3 with the LYS2 marker by targeted recombination of the J1.3LYS cassette is depicted on Parent YAC One. Replacement of the TRP1 marker with the HIS3 marker by targeted recombination of the YNNδγHIS cassette is depicted on Parent YAC Two. SpeI and NotI restriction sites are shown at the ends of the YAC inserts and are denoted "S" and "N" respectively. A fine structure restriction map of J1.3 is given in Choi et al., Nat. Genet. 4:117 (1993). The filled oval in the Sγ1-Cγ1 region fragment denotes the rat heavy chain 3' enhancer. Partial restriction maps of each input YAC as well as the resulting recombinant YAC products are presented.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The terms "substantially corresponds to", "substantially homologous", or "substantial identity" as used herein denotes a characteristic of a nucleic acid sequence, wherein a nucleic acid sequence has at least 70 percent sequence identity as compared to a reference sequence, typically at least 85 percent sequence identity, and preferably at least 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least 30 nucleotides long, and preferably at least 50 to 100 nucleotides long. "Substantially complementary" as used herein refers to a sequence that is complementary to a sequence that substantially corresponds to a reference sequence.

Specific hybridization is defined herein as the formation of hybrids between a targeting transgene sequence (e.g., a polynucleotide of the invention which may include substitutions, deletion, and/or additions) and a specific target DNA sequence (e.g., a human APP gene sequence or human immunoglobulin gene sequence), wherein a labeled targeting transgene sequence preferentially hybridizes to the target such that, for example, a single band corresponding to a restriction fragment of a gene can be identified on a Southern blot of DNA prepared from cells using said labeled targeting transgene sequence as a probe. It is evident that optimal hybridization conditions will vary depending upon the sequence composition and length(s) of the targeting transgene(s) and endogenous target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology*, Volume 152, Guide to Molecular Cloning Techniques (1987), Academic Press, Inc., San Diego, Calif., which are incorporated herein by reference).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "cognate" as used herein refers to a gene sequence that is evolutionarily and functionally related between species. For example but not limitation, in the human genome, the human immunoglobulin heavy chain gene locus is the cognate gene to the mouse immunoglobulin heavy chain gene locus, since the sequences and structures of these two genes indicate that they are highly homologous and both genes encode a protein which functions to bind antigens specifically.

As used herein, the term "xenogenic" is defined in relation to a recipient mammalian host cell or nonhuman animal and means that an amino acid sequence or polynucleotide sequence is not encoded by or present in, respectively, the naturally-occurring genome of the recipient mammalian host cell or nonhuman animal. Xenogenic DNA sequences are foreign DNA sequences; for example, human APP genes or immunoglobulin genes are xenogenic with respect to murine ES cells; also, for illustration, a human cystic fibrosis-associated CFTR allele is xenogenic with respect to a human cell line that is homozygous for wild-type (normal) CFTR alleles. Thus, a cloned murine nucleic acid sequence that has been mutated (e.g., by site directed mutagenesis) is xenogenic with respect to the murine genome from which the sequence was originally derived, if the mutated sequence does not naturally occur in the murine genome.

As used herein, a "heterologous gene" or "heterologous polynucleotide sequence" is defined in relation to the transgenic nonhuman organism producing such a gene product. A heterologous polypeptide, also referred to as a xenogeneic polypeptide, is defined as a polypeptide having an amino acid sequence or an encoding DNA sequence corresponding to that of a cognate gene found in an organism not consisting of the transgenic nonhuman animal. Thus, a transgenic mouse harboring a human APP gene can be described as harboring a heterologous APP gene. A transgenic mouse harboring a human immunoglobulin gene can be described as harboring a heterologous immunoglobulin gene. A transgene containing various gene segments encoding a heterologous protein sequence may be readily identified, e.g. by hybridization or DNA sequencing, as being from a species of organism other than the transgenic animal. For example, expression of human APP amino acid sequences may be detected in the transgenic nonhuman animals of the invention with antibodies specific for human APP epitopes encoded by human APP gene segments. A cognate heterologous gene refers to a corresponding gene from another species; thus, if murine APP is the reference, human APP is a cognate heterologous gene (as is porcine, ovine, or rat APP, along with APP genes from other species).

As used herein, the term "targeting construct" refers to a polynucleotide which comprises: (1) at least one homology region having a sequence that is substantially identical to or substantially complementary to a sequence present in a host cell endogenous gene locus, and (2) a targeting region which becomes integrated into a host cell endogenous gene locus by homologous recombination between a targeting construct homology region and said endogenous gene locus sequence. If the targeting construct is a "hit-and-run" or "in-and-out" type construct (Valancius and Smithies (1991) *Mol. Cell. Biol.* 11:1402; Donehower et al. (1992) *Nature* 356:215; (1991) *J. NIH Res.* 3:59; Hasty et al. (1991) *Nature* 350; 243, which are incorporated herein by reference), the targeting region is only transiently incorporated into the endogenous gene locus and is eliminated from the host genome by selection. A targeting region may comprise a sequence that is substantially homologous to an endogenous gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein, when referring to a targeting construct and an endogenous gene sequence, refer to a segment (i.e., a portion) of a targeting construct having a sequence that substantially corresponds to, or is substantially complementary to, a predetermined endogenous gene sequence, which can include sequences flanking said gene. When referring to homology regions shared between two YAC constructs, "homology region" refers to a segment of one YAC construct that substantially corresponds to, or is substantially complementary to, a region on the second YAC construct. A homology region is generally at least about 100 nucleotides long, preferably at least about 250 to 500 nucleotides long, more preferably at least about 1000 nucleotides long, or preferably longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The terms "homology clamp" and "homology region" are interchangeable as used herein, and the alternative terminology is offered for clarity, in view of the inconsistent usage of similar terms in the art. A homology clamp does not necessarily connote formation of a base-paired hybrid structure with an endogenous sequence. Endogenous gene sequences that substantially correspond to, or are substantially complementary to, a transgene homology region are referred to herein as "crossover target sequences" or "endogenous target sequences."

As used herein, the term "minigene" or "minilocus" refers to a heterologous gene construct wherein one or more nonessential segments of a gene are deleted with respect to the naturally-occurring gene. Typically, deleted segments are intronic sequences of at least about 100 basepairs to several kilobases, and may span up to several tens of kilobases or more. Isolation and manipulation of large (i.e., greater than about 50 kilobases) targeting constructs is frequently difficult and may reduce the efficiency of transferring the targeting construct into a host cell. Thus, it is frequently desirable to reduce the size of a targeting construct by deleting one or more nonessential portions of the gene. Typically, intronic sequences that do not encompass essential regulatory elements may be deleted. For example, a human immunoglobulin heavy chain minigene may comprise a deletion of an intronic segment between the J gene segments and the μ constant region exons of the human heavy chain immunoglobulin gene locus while retaining important regulatory elements in that region. In an additional example of a minigene, a human APP minigene can comprise the spliced exons 1 to 10 of human APP (obtained from a CDNA, thus having introns removed) joined to exons 11 to 18 obtained from APP genomic DNA. Frequently, if convenient restriction sites bound a nonessential intronic sequence of a cloned gene sequence, a deletion of the intronic sequence may be produced by: (1) digesting the cloned DNA with the appropriate restriction enzymes, (2) separating the restriction fragments (e.g., by electrophoresis), (3) isolating the restriction fragments encompassing the essential exons and regulatory elements, and (4) ligating the isolated restriction fragments to form a minigene wherein the exons are in the same linear order as is present in the germline copy of the naturally-occurring gene. Alternate methods for producing a minigene will be apparent to those of skill in the art (e.g., ligation of partial genomic clones which encompass essential exons but which lack portions of intronic sequence). Most typically, the gene segments comprising a minigene will be arranged in the same linear order as is present in the germline gene, however, this will not always be the case. Some desired regulatory elements (e.g., enhancers, silencers) may be relatively position-insensitive, so that the regulatory element will function correctly even if positioned differently in a minigene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a minigene. Similarly, some genes may have exons which are alternatively spliced at the RNA level, and thus a minigene may have fewer exons and/or exons in a different linear order than the corresponding germline gene and still encode a functional gene product. A cDNA encoding a gene product may also be used to construct a minigene. However, since it is generally desirable that the heterologous minigene be expressed similarly to the cognate naturally-occurring nonhuman gene, transcription of a cDNA minigene typically is driven by a linked gene promoter and enhancer from the naturally-occurring gene.

As used herein, the term "large transgene" or "large homologous targeting construct" generally refers to polynucleotides that are larger than 50 kb, usually larger than 100 kb, frequently larger than 260 kb, occasionally as large as 500 kb, and sometimes as large as 1000 kb or larger.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., lipofection protocols). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference).

Oligonucleotides can be synthesized on an Applied Biosystems, Inc. (Foster City, Calif.) oligonucleotide synthesizer according to specifications provided by the manufacturer.

It has often been observed that cDNA-based transgenes are poorly expressed or inappropriately regulated. Genomic DNA-based transgenes (i.e., constructed from cloned genomic DNA sequences) which substantially retain the content and organization of the naturally-occurring gene locus are more likely to be correctly expressed, but are limited in size by the cloning capacity of bacteriophage and plasmid/cosmid vectors. The yeast artificial chromosome (YAC) is a recently developed cloning vehicle with a capacity of at least approximately 2 megabases (Mb) (Burke et al. (1987) *Science* 236:806). An upper size limit has not been determined to date. The ability to reproducibly and efficiently introduce YACs into transgenic mice can significantly surpass current transgene size limits. Methods used herein for YAC cloning, manipulation and genetic modification are those well known and commonly employed in the art. See for example, U.S. Pat. No. 4,889,806 and WO 94/00569. Basic methods of yeast genetics, including descriptions of selectable markers and selective media, are found in Methods In Enzymology (1991) Vol. 194, Academic Press, Inc. Additional methods can be found in Current Protocols in Molecular Biology, ed., Ausubel (1994), Greene Pub. Associates and Wiley—Interscience, J. Wiley, New York, N.Y., particularly volume 2 chapter 13 "Growth and Manipulation of Yeast"; all volumes of which are hereby incorporated by reference.

It is an object of the present invention to provide methods for constructing large DNA constructs as Yeast Artificial Chromosomes by homologous recombination between YACs (referred to as parental or input YACs) during meiosis in yeast. In general, homologous recombination between a pair of YACs that share a region of homology is obtained from a three step process: by first mating yeast cells of opposite mating types, where each type contains one YAC of the YAC pair to be recombined, to form a diploid that contains both input YACs, then sporulating the diploid, i.e. inducing the diploid to undergo meiotic division and haploid spore formation, usually by nitrogen starvation, during which recombination between the YAC pair can occur, and subsequently identifying (and isolating) those haploid spores bearing a desired recombinant YAC. Although the invention can be applied to recombination between any YAC pair sharing relatively large regions of homology or between a YAC pair displaying mitotic stability when co-propagated in a diploid, the methods of the invention find particular use when applied to YAC pairs with homology regions of less than about 50 kb, preferably less than about 40 kb, more preferably less than about 20 kb, even more preferably less than about 10 kb, and most preferably less than 5 kb. The methods of the invention find particular use when applied to YAC pairs that display mitotic incompatibility when attempts are made to co-propagate them in a diploid. The methods of the invention are particularly useful with YAC pairs having both limited homology regions as described above and mitotic incompatibility. Accordingly, it is an object of the invention to provide methods that increase the frequency of haploid yeast spores containing the desired recombinant YAC after the sporulation step, and to provide methods that select preferentially for desired haploid cells from the spore population to thus increase the frequency of desired cells within the population of cells to be analyzed for the presence of the desired recombinant YAC. According to the invention, methods, which include steps for construction of diploids prior to sporulation and steps for subsequent genetic selection of YAC containing spores, which steps can be used separately or, most preferably, in combination to best achieve the foregoing objects.

According to the invention methods for diploid construction are provided such that during the mating step a diploid yeast cell, containing a pair of parent (or input) YACs that share a homology region suitable to enable homologous recombination between them during meiosis, will maintain both input YACs without rearrangements upon entering the sporulation step. This is accomplished by minimizing or preventing diploid growth, i.e. mitotic division (doubling) of the diploid cell, immediately after the mating, during the mating step. A method of producing a recombinant YAC is provided that includes the steps of (a) mating a first haploid yeast cell comprising a first YAC to a second haploid yeast cell comprising a second YAC having a homology region with the first YAC, to obtain a diploid yeast cell, wherein mitotic doubling of the diploid is limited or prevented, (b) sporulating the diploid and/or its mitotic progeny, to obtain spores, and then (c) identifying spores that comprise the recombinant YAC. Alternatively the method includes the steps of (a) mating a first haploid yeast cell comprising a first YAC to a second haploid yeast cell comprising a second YAC having a homology region with the first YAC to obtain a diploid yeast cell, (b) sporulating the diploid and/or its mitotic progeny to obtain spores, and then (c) identifying spores that comprise the recombinant YAC by culturing spores for growth of spores comprising the recombinant YAC, and optionally, selecting against spores that comprise a parental YAC(s) and/or an undesired recombinant YAC. When limited diploid growth during the mating step is desired (for example, as in the case when a particular YAC pair is mitotically incompatible), it is limited to about 8 or fewer diploid doublings, preferably to 6 or fewer doublings, more preferably to about 5 or fewer, even more preferably to 3 or fewer doublings, or most preferably prevented. Diploid doubling during the mating step can be delayed, slowed, limited or prevented by monitoring the doubling during the mating step, by chemical means, by genetic means, by culturing conditions that favor mating but disfavor mitotic growth, by limiting the time of the mating event, by limiting the time of diploid growth, and by altering the temperature during growth. For example, mutant haploid yeast cells can be used whose entry into mitosis can be selectively controlled, for example by a change in temperature. Or for example, haploids having the same auxotrophy can be separately pre-grown in medium providing the needed nutritional supplement, such that they would internally accumulate the nutritional supplement, and then the cells are mixed together for mating on auxotrophic media (lacking the nutritional supplement) such that the cells would have a sufficient internal amount of the nutritional supplement to allow mating but not subsequent diploid growth (or at least growth). More specifically, for example, YAC-bearing haploids, each leu2$^-$, are separately pre-grown in leucine-containing medium and allowed to accumulate leucine, and then transferred to leucine-lacking medium for the mating step. Drug sensitivity based control can also be used. When mass matings, (i.e. mixing of cultures of the parental haploid yeast cells, preferably between $10^7$ to $10^8$ cells of each type are performed, diploid mitotic growth can, for example, be readily limited by limiting the mating step to a period of time equal to or less than about 8 diploid-doubling times, preferably to 6 or fewer doubling times, more preferably to about 5 or fewer, even more preferably to 3 or fewer doubling times, or most preferably prevented. By "mating step" is meant to the period of time commencing with the mixing of cells of each mating type, including a lag period prior to schmoo formation, and including diploid mitotic growth that may occur when non-synchronously mating cells are used. Diploid doubling time under the conditions of mating can be routinely determined by using standard protocols found in the art. Most, preferably mating is performed in the absence of selection for markers located on the YAC arms. This lack of selection for the desired diploid runs counter-intuitive to established yeast mating procedures. As has been discovered by the present inventors, application of genetic selection for diploids containing both YACs, such as by selection for markers on the YACs' arms, surprisingly resulted in the outgrowth of diploids in which undesirable rearrangements of the YACs had occurred. However, as taught herein, the counter-intuitive absence of a selection for markers on the YACs' arms prior to sporulation circumvents the problems caused by undesirable rearrangements. Although 30° is a temperature typically used for yeast culturing, diploid growth can also be limited during the mating step by performing the initial period of mating at a higher temperature than the remaining period. The initial high temperature period includes a period for the haploid parental cell to form a "schmoo." The period can be determined by monitoring the cells, preferably microscopically, for the appearance of "schmoos". Subsequently, mating cells are transferred to a lower temperature, at which cell fusion and conjugation continues but mitotic division is relatively retarded compared to the higher temperature. An upper temperature for the initial period is limited by its toxicity to the yeast cells. A lower temperature is limited by its toxicity to cells or prevention of conjugation. When desired a preferred temperature range for the initial mating period is about 25° to about 35° C., more preferably about 28° to 32° C., and most preferably about 30° C. A preferred temperature for the remaining period of mating is about 15° to 25° C., more preferably about 18° to 22° C., and more preferably about 20° C. In one specific embodiment of the invention mating is monitored for several hours to overnight, such that mating is complete, or nearly complete, but diploid growth is limited to zero to three generations as follows. Approximately $5\times10^7$ to $10^8$ cells of a MATa strain is mixed with an approximately equal number of cells of a MATα strain, vortexed, and bulk plated as an approximately dime-sized drop onto a 10 cm YPD plate. After four hours at 30° C., the patch is evenly spread out over the entire surface of the YPD plate and kept at room temperature (about 20°–25° C.) overnight (about 18–24 hours). This particular procedure results in efficient mating with approximately one to three generations of diploid growth. One can readily adjust the time periods, temperature or other conditions consistent with the mating and diploid growth rates for a particular combination of haploids.

Recombination (meiotic recombination) can then be induced by sporulating the diploid. Standard sporulation routines can be used, with the proviso that further diploid growth is not encouraged. The resulting sporulated culture is then enriched for spores using known protocols. Enrichment will result in a substantially pure spore population. By substantially pure is meant about 90% spores to about 10% diploids and unmated haploids progressing to a more preferred about 95% to 5%, to an even more preferred about 99% to about 1%, to ideally about 100% spore population. Although any standard sporulation protocol can be followed, a preferred protocol includes removing about $10^8$ cells from the mating plate, washing the cells in sterile water, resuspending the washed cells in 10 mls of sporulation medium, and incubating the cells at 30° C. for three to five days. Several findings regarding sporulation efficiency emerged from these experiments. First, sporulation efficiency drops off dramatically when the culture density exceeds $5\times10^7$/ml. Second, maintenance of sporulation cultures in polyethylene tubes effectively precludes sporulation. Best efficiencies were obtained in polystyrene or glass tubes. A preferred sporulation medium is 1% potassium acetate supplemented with one-fourth of the normal amounts of amino acids (Rose et al. (1990) Methods in Yeast Genetics: A Laboratory Course Manual, 1990 Edition, Cold Spring Harbor Laboratory Press, which is hereby incorporated by reference in its entirety.) although other standard yeast sporulation, particularly for *S. cerevisiae*, will suffice. The spores can be screened by the usual methods in the art for the desired recombinant YAC, or preferably, a method of genetic selection according to the invention, as presented below, is followed in which case step (c) includes identifying spores that comprise the desired recombinant YAC by culturing spores under conditions that select for growth of spores comprising the recombinant YAC, and optionally, that select against spores that comprise the undesired recombinant YAC and/or one or both unrecombined parental YACs in order to select for and enhance identification of spores containing the desired YAC.

Methods are provided for the spore analysis step that facilitate detection and identification of spores having the desired recombinant YAC by performing a genetic selection for yeast spores containing the desired recombinant YAC, while optionally counter-selecting (i.e. selecting against) for the undesired by-product recombinant YAC and/or one or both parental YACs. Genetic selection is designed based upon the expected selectable markers present on the desired recombinant YAC in comparison to those present on the byproduct recombinant YAC and/or one or both parental YACs. According to the invention, genetic selection is performed by providing the input YACs with selectable markers such that YAC recombination results in the desired recombinant YAC predictably having a certain selectable marker, or preferably markers, that allow application selection conditions for the marker or markers to obtain preferential growth of spore progeny containing the desired YAC in the presence of spores containing a YAC having a different selectable marker or markers, and optionally, to select against the marker or markers present on the undesired recombinant YAC and/or one or both parental YACs. After diploid construction, preferably by a method of diploid construction according to the present invention, and sporulation, spores are enriched with respect to diploids and unmated haploids by methods known in the art, and the enriched spore population is subjected to genetic selection in media that selects for the desired recombinant YAC and, optionally but preferably, counter-selects for haploids bearing the undesired recombinant YACs and haploids bearing either parental YAC. The selection step can be designed to select for at least one selectable marker present on the desired recombinant YAC, and more preferably for at least two selectable markers that are present on the desired recombinant YAC but that are not present on the undesired recombinant YAC. More preferably counter-selection is also employed for cells with either the undesired recombinant YAC and cells with one of the parental YACs. Most preferably, counter-selection results in cell death. Any selectable genetic marker or combination of markers can be used so long as a genetic selection can be designed for the marker that selects for growth of cells containing the desired YAC, and so long as the genetic selection for each marker is not mutually exclusive when used in combination (or with a counter-selection). Auxotrophic markers are preferred for ease of use, although drug resistance, metal (toxin) tolerance markers and the like can also be used. Commonly used, and preferred, markers in yeast are URA3, TRP1, LEU2, LYS2, ADE2 and HIS3. Preferably, although not necessarily, marker selection occurs concomitantly, rather than sequentially. Markers that find use in counter-selection are those known in the art and include URA3, and LYS2. Preferred is the URA3 marker in which 5-fluoro-orotic acid ("FOA") supplementation to the media (Boeke et al. (1984) Mol. Gen. Genet. 197:345) results in the death of cells bearing a genomic, plasmid-borne, or YAC-borne wildtype URA3 gene. Also preferred is LYS2 which also has a counterselection scheme. The chemical alpha-amino adipate is used to select against LYS2, as the LYS2 gene product processes it to a toxic product. Yeast haploid strains preferably have non-reverting mutations, .e.g. disrupted null mutations, in the markers of interest in order to minimize background false positives. Most preferably it is desirable not to have suppressible or revertible mutant alleles in the backgrounds, since there will be false positives coming from suppressors and, less likely, revertants. Nonreverting alleles like deletions/insertions are preferable to suppressible alleles like amber or ochre mutations or frameshifts. As a consequence of the method of the invention, the resulting surviving cell population has an increased frequency of haploid cells containing the desired YAC, and accordingly, the subsequent screening and analysis for cells harboring the desired recombinant YAC is greatly simplified and expedited.

If the input YACs exhibit mitotic stability in the parental haploid strains, the strains are typically expanded in selective liquid medium (selective for the input YAC), and only one clonal population of each parent need be used for mating. In the case where an input YAC (or both input YACs) may exhibit some mitotic instability in the parental haploid state, multiple subclones of each of the two haploid YAC strain can be grown non-selectively to a large patch with subsequent mating by mixing a fraction of each patch to all possible mates. Then, if desired, while the cultures are in sporulation medium, the parental (haploid) subclones can be screened by pulsed field gel electrophoresis to identify the subclone of each mating type exhibiting minimal YAC loss. Purified spores from the cross between these two haploid subclones are chosen for the genetic selection step of the invention in which one selects for the recombinant YAC and optionally against the undesired by-product recombinant YAC and one or both parental unrecombinant YACs. Note that the % YAC loss of a subclone patch is a statistical property of the patch and not a genetic property of the subclone, i.e., a low % loss patch will display a distribution of % loss in its subclones. The distribution of % loss is dependent on the mitotic stability of the particular YAC. A very unstable YAC will require screening of many more subclones than a stable YAC to identify a patch with sufficiently low % YAC loss.

Although either the step of minimization of diploid mitotic growth or the step of genetic selection, preferably selection for the desired recombinant YAC and against the undesired YACs, can be performed without the other as a step in a known YAC recombination protocol, in the most preferred embodiment of the invention both steps are performed. Consequently, recombination of unstable YACs comprising short regions of homology can be more readily obtained by the present invention.

The invention finds particular use in constructing large DNA constructs of transgenes and large homologous targeting constructs spanning at least one complete transcriptional complex, suitable for transfer into mammalian cells, such as embryonic stem ("ES") cells, typically for construction of a transgenie animal.

Unrearranged immunoglobulin genes cloned in YACs can be introduced into ES cells and developed to form a transgenic animal in which productive VDJ rearrangement occurs, and expression of immunoglobulin chains also occurs. Large transgenes can be cloned in YACs and, after isolation from the host yeast cells, efficiently transferred into mammalian cells (e.g., ES cells) without prior separation of the desired transgene sequences from yeast-derived YAC sequences, and that the presence of such yeast-derived YAC sequences can be non-interfering (i.e., compatible with efficient transgene integration and transcription of a transgene transcriptional unit). The present methods may also be carried out with somatic cells, such as epithelial cells (e.g., keratinocytes), endothelial cells, hematopoietic cells, and myocytes, for example. A large transgene can be nonhomologously integrated into a chromosomal location of the host genome. Alternatively, a homologous targeting construct (which may comprise a transgene) that contains at least one altered copy of a portion of a germline gene or a xenogenic cognate gene (including heterologous genes) can be introduced into the genome of embryonic stem cells. In a portion of the cells, the introduced DNA is either nonhomologously integrated into a chromosomal location or homologously recombines with the endogenous (i.e., naturally occurring) copy of the mouse gene, replacing it with the altered construct. Cells containing the newly engineered genetic sequence(s) are injected into a host mouse blastocyst, which is reimplanted into a recipient female. Some of these embryos develop into chimeric mice that possess a population of germ cells partially derived from the mutant cell line. Therefore, by breeding the chimeric mice it is possible to obtain a new line of mice containing the introduced genetic lesion (reviewed by Capecchi et al. (1989) *Science* 244:1288, incorporated herein by reference).

For homologous targeting constructs, targeting efficiency generally increases with the length of the targeting transgene portion (i.e., homology region) that is substantially complementary to a reference sequence present in the target DNA (i.e., crossover target sequence). In general, targeting efficiency is optimized with the use of isogenic DNA homology regions, although it is recognized that the presence of recombinases in certain ES cell clones may reduce the degree of sequence identity required for efficient recombination.

Transgenes which encode a gene product that is xenogenic (e.g., heterologous) to a nonhuman host species are useful. Such transgenes typically comprise a structural gene sequence expression cassette, wherein a linked promoter and, preferably, an enhancer drive expression of structural sequences encoding a xenogenic (e.g., heterologous protein). The polynucleotide sequence encoding the xenogenic (e.g., heterologous) protein can be operably linked to cis-acting transcriptional regulatory regions (e.g., promoter, enhancer) so that a heterologous protein is expressed in a manner similar to the expression of the cognate endogenous gene in the naturally-occurring nonhuman animal.

The present invention thus finds particular use in constructing YACs, generally by recombination of YACs obtained from genomic libraries but also by recombination with a genetically engineered YAC designed to provide desired mammalian cell selectable markers, expression regulatory regions, protein fusions, larger regions for homologous targeting, and the like.

The methods of the present invention find particular use in constructing minigenes that comprise clusters of genes that are not normally found clustered in a genome or that are located in different genomes. In many instances single components of a multicomponent complex, a metabolic pathway, or a regulatory pathway, e.g. immunomodulation, are encoded on separate genes, but all of the components, and thus all of the genes, are needed or desired to enhance or obtain function. One such group would be human cytokines which find use to support the development of transplanted human hematopoietic cells in a mouse. Of the dozens of cytokines characterized, only a few are naturally clustered. Prior to the methods of the present invention, typically each cytokine gene of interest for obtaining desired function would be used to create a separate transgenic line, which lines would then be interbreed to obtain a desired line having all of the cytokine transgenes of interest. In addition to the time and labor required to concomitantly generate, select, and maintain a mouse line(s) for each gene, approximately one year of interbreeding would be required to obtain the final desired line (in the case where about 5 genes were used). Although it has been reported that coinjection of separate genes (up to at least 5 genes) may result in integration at the same site (and thus be genetically linked to each other), this approach has problems. First, the cointegrated transgene arrays would be unpredictable and uncontrollable in structure. Consequently, the stoichiometry of the component genes of the transgene array could not be controlled, and in addition, subsequent structural analysis of the transgene array would be very difficult if not impossible. Second, it is desirable to use genomic fragments of sufficient size such that each gene is authentically regulated. That is, by adjoining small transgenes (e.g. less than 30 kb) it is highly likely that they would affect each others' regulation. By adjoining large genomic fragments, e.g. about 100 kb, each gene would be better buffered from each other with respect to interfering with gene regulation. Genomic P1 clones (carrying inserts of about 75–100 kb) are an ideal source of such large genomic fragments. The P1 cloning system is based on a modified P1 phage replicon as vector. The salient feature is that the insert size range is about 75–100 kb. Also a screening service for a human genomic P1 library is available (Genome Systems, St. Louis, Mo.). If P1 DNAs are microinjected, restrictions on the amount of DNA which is microinjectable would limit the number of copies of each gene in the microinjected DNA mixture. On the other hand, the cloning capacity of YACs permits the construction of a single transgene containing all the cytokine genes of interest, at least 5 in this example. Using the method of the present invention, one would first obtain P1 clones (approximately 100 kb each) each containing one of the genes of interest, convert these P1 clones to individual YACs, construct "linking" YACs containing inserts derived from a small fragment of DNA from each of two individual genes or regions to be adjoined, and then applying the homologous recombination methods of the present invention to sequentially recombine YACs in the desired order to obtain a final recombinant YAC comprising the desired transgene array. Linking YACs are employed by first recombining by the methods of the present invention a linking YAC with a first YAC containing one of two genes of interest to be adjoined. A linking YAC contains as its DNA insert a first small region that is homologous with a portion of the first gene of interest and a second small region that is homologous with a portion of the second gene of interest. As a consequence of the homologous recombination between the linking YAC and the first YAC driven by the first small region of homology, the desired first recombinant YAC contains the first gene of interest plus the second small region of homology (to the second gene of interest). Consequently, a second homologous recombination, between the first recombinant YAC and a second YAC that contains the second gene of interest for adjoining, will be driven by the second small region of homology, and by using the methods of the invention will thus result in a obtaining a desired second recombinant YAC in which the first and second genes are adjoined.

The DNA inserts for linking YACs can be conveniently constructed in plasmid/phagemid/cosmid systems well known in the art using standard molecular biology techniques. Since these convenient systems typically allow manipulation only of relatively small fragments of DNA, the linking YACs will in turn contain small inserts; the inserts of the linking YACs will thus only share small regions of homology for recombination with larger YACs that contain the genes of interest for adjoining. Consequently, the methods of the invention find particular use when linking YACs are employed, since the methods enable obtaining a desired recombinant YAC resulting from recombination of YACs sharing a relatively small region of homology as taught herein. Of course, the methods find particular use in recombination schemes that typically result in a relatively low recombination frequency, such as when a multiple, preferably three-way, recombination event is attempted or when short homology regions are relied upon for homologous recombination (as when using linking YACs).

Methods of the invention are provided for the construction of linking YACs by long-range polymerase chain reaction ("LR-PCR"). LR-PCR allows for amplification of a homology region obtained from a first YAC such that the amplified DNA can be ligated to a second LR-PCR amplified homology region obtained from a second YAC, followed by ligation of the adjoined DNA to the arms of a YAC vector to create the linking YAC.

The vectors containing the homology regions for adjoining in order to construct a linking YAC can be obtained by digestion of the first and second YAC DNA at a restriction site which occurs only once in the vector arm, e.g. XhoI and NdeI for the centromeric arm and XhoI and EcoRV for the acentromeric arm. The digestion products are ligated under conditions promoting circularization of the DNA fragments. The ligation products are introduced into *E. coli* by electroporation or any other convenient transformation method. The centromeric vector can be isolated by selection for ampicillin resistance. If the YAC is cloned in a YAC vector containing a kanamycin resistance marker on the acentromeric arm (such as pYACneo), the acentromeric vector can be isolated by selection for kanamycin resistance. Other selection schemes can be used as are known in the art and as are appropriate for the markers on a particular YAC vector. Alternatively, the first and second YAC DNA ligation products can be used directly for LR-PCR isolation of the homology regions.

The primers for LR-PCR isolation of YAC homology regions are designed to hybridize to sequences near the ends of the YAC vector to minimize the amount of YAC vector sequences in the amplification product. Each primer consists of a 3' region of preferably approximately 20 bp containing homology to the YAC vector arm and a 5' region preferably of approximately 20 bp containing at least one restriction site. The first and fourth primers (for example, S3CX and S1AR respectively in FIG. 9A) have at least one restriction site in common, and the second and third primers (for example, S2CR1 and S2'AX1 respectively in FIG. 9A) have in common at least one restriction site which differs from that found in the first and fourth primers. The restriction site of the first and fourth primers is chosen such that it does not occur within either homology region and is found as a cloning site of the YAC vector that comprises the linking YAC. The restriction site of the second and third primers are chosen such that it does not occur within either homology region or within the YAC vector arm sequences. Alternatively, the restriction site sequences can exist in the primers as pre-cut regions with appropriate overhang for subsequent ligation. The suitable size of the primer region binding to a vector for use in LR-PCR is well-known known in the art, but preferably is at least about 14 bp, more preferably about 20 bp, to about 35 base pair. The primer regions containing the primer restriction sites used for subsequent fragment ligation and ligation to the YAC arms, need not be, are likely not homologous to the vector sequence but are rather synthetic regions designed to harbor the appropriate restriction sites.

Figure 9A:
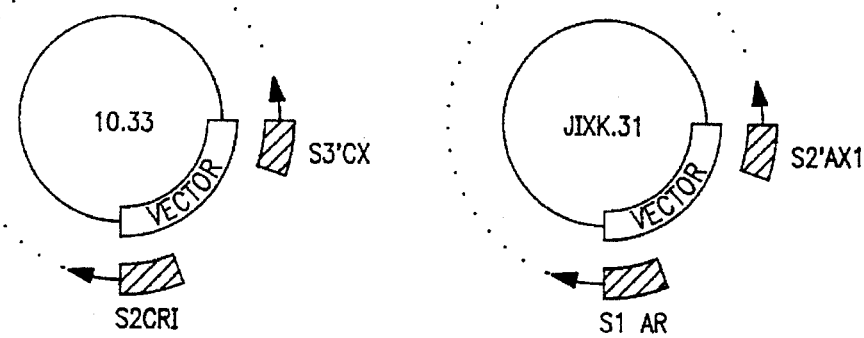
FIG. 9A and FIG. 9B depict construction of a linking YAC insert by LR-PCR.
Figure 9B:
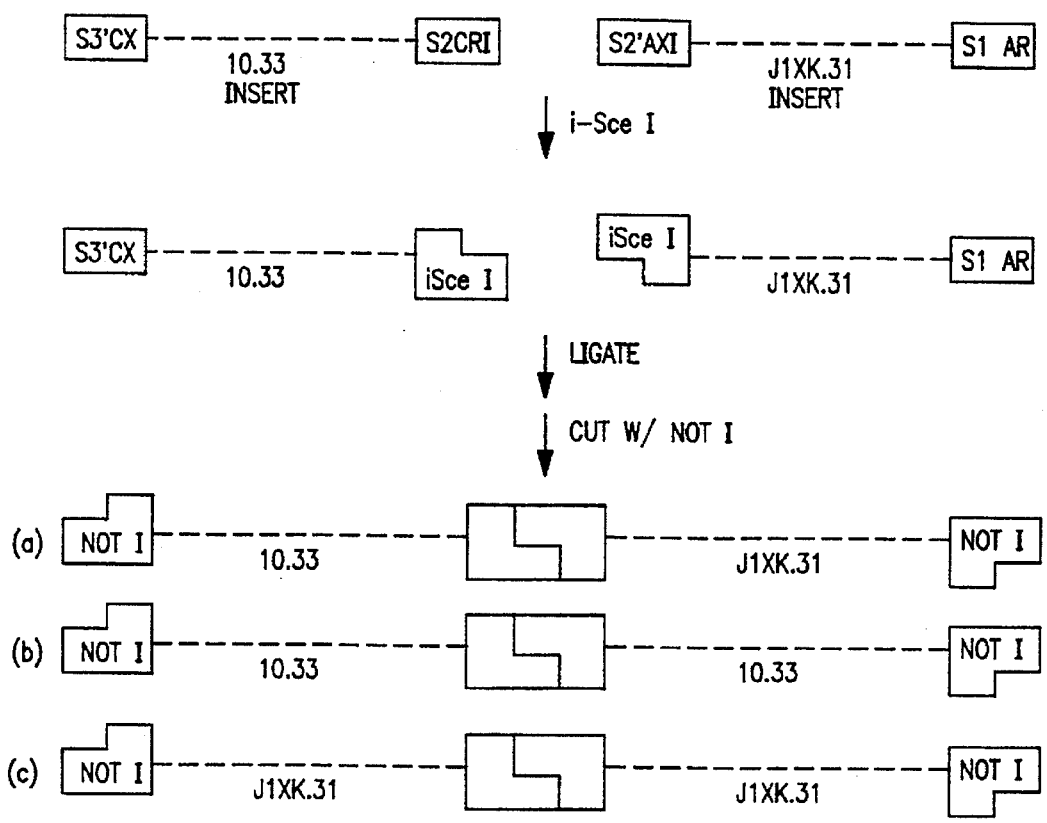

The first and second primers are used to amplify the homology region of the first vector and the third and fourth primers are used to amplify the homology region of the second vector. The desired amplification products are purified by gel electrophoresis and/or ethanol precipitation and digested at the common restriction site of the second and third primers with the appropriate restriction enzyme. The digestion products are purified by preparative gel electrophoresis, mixed at a 1:1 molar ratio, and ligated. The ligation products are then digested at the restriction site of the first and fourth primer, and the digestion products isolated and purified by preparative gel electrophoresis. The digestion products are predominantly comprised of three dimeric DNA fragments: the desired heterodimer wherein the downstream end of the first homology region is ligated to the upstream end of the second homology region, the homodimer of the first homology region and the homodimer of the second homology region. The DNA products are then ligated to YAC vector arms at the cloning site compatible with the restriction site of the first and fourth primers, and the ligation mix is introduced into a yeast host strain by yeast transformation. The desired linking YAC containing the heterodimer in the same vector arm orientation as the parent YACs is identified among the transformant clones by restriction digest southern analysis. If the two homology regions differ in size, the heterodimer can be isolated away from the homodimers by preparative gel electrophoresis prior to ligation to YAC vector arms, enriching for the desired linking YAC. FIG. 9A and FIG. 9B illustrate the use of LR-PCR for linking YAC construction and provides one specific embodiment. Although NotI restriction enzyme sites are exemplified herein, any other rare restriction enzyme site can be used, more preferably one that does not appear in the human genome, with the proviso that it does not appear in the YAC vector arms or in either homology region. Although i-SceI is exemplified herein, any other rare restriction enzyme site can be used, more preferably one that does not appear in the human genome, with the proviso that it not be present in the YAC vector arms or either region of homology.

Large polynucleotides are usually cloned in YAC vectors. For example, human genomic DNA libraries in YAC cloning vectors can be screened (e.g., by PCR or labeled polynucleotide probe hybridization) to isolate YAC clones spanning complete genes of interest (e.g., a human APP gene, a human immunoglobulin heavy chain locus or light chain locus), or significant portions of such genes which comprise a complete transcriptional unit. Methods for making YAC libraries, isolating desired YAC clones, and purifying YAC DNA are described in the art (U.S. Pat. No. 4,889,806; Burke et al. (1987) *Science* 236 806; Murry et al. (1986) *Cell* 45:529, incorporated herein by reference).

Genes and DNA regions of interest, as well as YAC vectors, for use in the methods and compositions of the present invention include those reported in: Lonberg et al. (1994) *Nature* 368:856–859); Chen et at. (1993) *Internat. Immunol.* 5:647–656: Taylor et al. (1993) *Internat. Immunol.* 6:579–591; Choi et al. (1993) *Nature Genetics* 4:117–123; Chen et al. (1993) *Embo J.* 3:821–830; Pearson and Choi (1993) *Proc. Natl. Sci.* 90:10578–10582; and Taylor et al. (1992) *Nucl. Acids Res.* 20:6287–6295, as well as in application U.S. patent application Ser. No. 08/148,177 filed Nov. 5, 1993, and U.S. patent application Ser. No. 07/900,972, filed Jun. 18, 1992, all of which are hereby incorporated by reference. These same references provide and discuss methods useful for the introduction into host cells of the large DNAs produced by the methods of the present invention.

Once a desired YAC clone is isolated, and preferably deproteinized, yeast-derived YAC sequences may optionally be completely or partially removed by digestion with one or more restriction enzymes which cut outside the desired cloned large transgene sequence; yeast-derived sequences are separated from the cloned insert sequences by, for example, pulsed gel electrophoresis. Preferably, a complete unrearranged YAC clone is used as a large transgene or large homologous targeting construct in the methods of the invention.

Preferred YAC clones are typically those which completely or partially span large structural gene sequences for example, human APP gene, human immunoglobulin heavy chain locus, human immunoglobulin light chain locus, human α1-antitrypsin gene, human Duchenne muscular dystrophy gene, human Huntington's chorea-associated loci, and other large structural genes, preferably human genes.

A modified pYAC3 vector (Burke et al. (1987) *op. cit.*, incorporated herein by reference), pYACneo (Traver et al. (1989) *Proc. Natl. Acad. Sci.* (*U.S.A.*) 86:5898, incorporated herein by reference), and pCGS966 (Smith et at. (1990) *Proc. Natl. Acad. Sci.* (*U.S.A.*) 87:8242, incorporated herein by reference) are YAC useful cloning vectors.

YAC clones comprising a large heterologous transgene find use, for example, in methods to transfer the large transgene into a pluripotent stem cell line which can be used to generate transgenic nonhuman animals following injection into a host blastocyst. For example, WO 94/00569 reports successful transfer into mouse ES cells of the human APP transgene carried on a YAC clone. Correctly targeted ES cells are then transferred into suitable blastocyst hosts for generation of chimeric transgenic animals according to methods known in the art (Capecchi, M. (1989) *TIG* 5:70; Capecchi, M. (1989) *Science* 244:1288, incorporated herein by reference). Several studies have already used PCR to successfully identify the desired transfected cell lines (Zimmer and Gruss (1989) *Nature* 338:150; Mouellic et al. (1990) *Proc. Natl. Acad. Sci.* (*U.S.A.*) 87:4712; Shesely et al. (1991) *Proc. Natl. Acad. Sci. USA* 88:4294, which are incorporated herein by reference). This approach is very effective when the number of cells receiving exogenous targeting transgene(s) is high (i.e., with electroporation or lipofection) and the treated cell populations are allowed to expand (Capecchi, M. (1989) *op. cit.*, incorporated herein by reference). The blastocysts containing the injected ES cells are allowed to develop in the uteri of pseudopregnant nonhuman females and are born as chimeric mice. The resultant transgenic mice are chimeric for cells having the large transgene(s)/homologous targeting constructs and are backcrossed and screened for the presence of the transgene (s) and/or YAC sequences by PCR or Southern blot analysis on tail biopsy DNA of offspring so as to identify transgenic mice heterozygous for the transgene(s)/homologous targeting constructs. By performing the appropriate crosses, one can produce a transgenic nonhuman animal homozygous for multiple large transgenes/homologous recombination constructs, and optionally also for a transgene encoding a different heterologous protein. Such transgenic animals are satisfactory experimental models for various diseases linked to the transferred transgene(s).

The YAC recombinant products of the invention find additional use in the production in a host cell of recombinant proteins and recombinant multi-protein complexes, and in the concomitant production of proteins involved in a biological pathway or other biological process. The recombinant YACs of the invention are useful for expression of heterologous recombinant protein or proteins in a yeast host cell (or other host cell transformed with a YAC or large DNA produced by the methods of the invention) for uses including subsequent preparation and isolation of the recombinant proteins, particularly isolation of complexes that previously would be prepared by separate expression and isolation of the components from different cells followed by in vitro assembly of the complex. Biological pathways involving multiple proteins or gene products can be reconstructed in a host cell by use of the large multi-gene DNAs that can be readily constructed by the methods of the invention. Such host cells, such as YAC containing yeasts, are useful as factories to produce a product or products of the biological pathway of interest. In addition, the methods of the invention provide large multi-gene DNAs that find use to reconstruct a biological pathway in the transformed host cell in order to facilitate the study of complex biological pathways and their components by enabling the use of powerful genetic and molecular biology approaches, such as mutational analyses.

EXAMPLES

Figure 2:
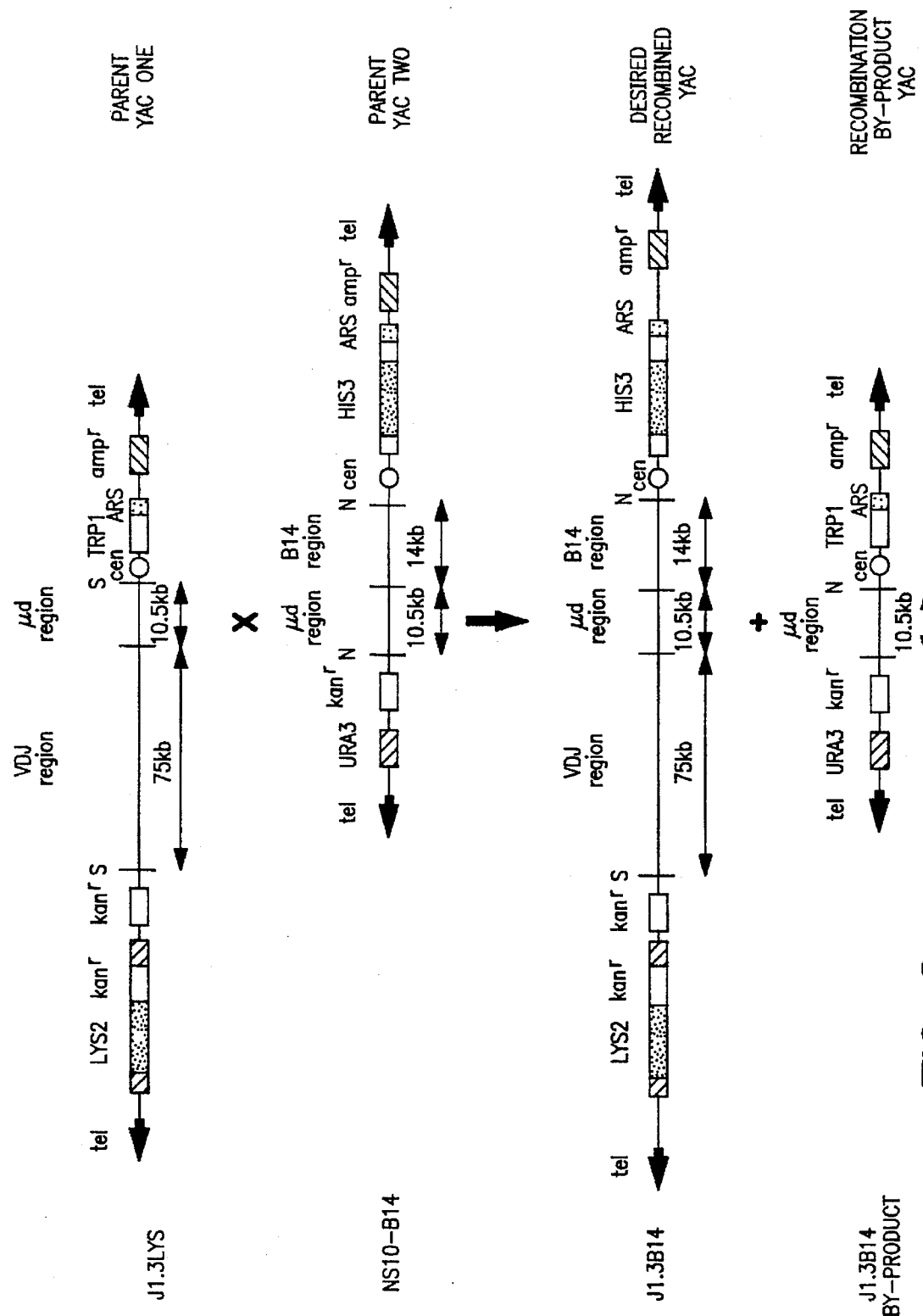
FIG. 2 is a schematic depicting recombination between YAC pairs J1.3LYS and NS10-B14. Partial restriction maps of each input YAC as well as the resulting recombinant YAC products are presented. NS10-B14 is a linking YAC.
Figure 3:
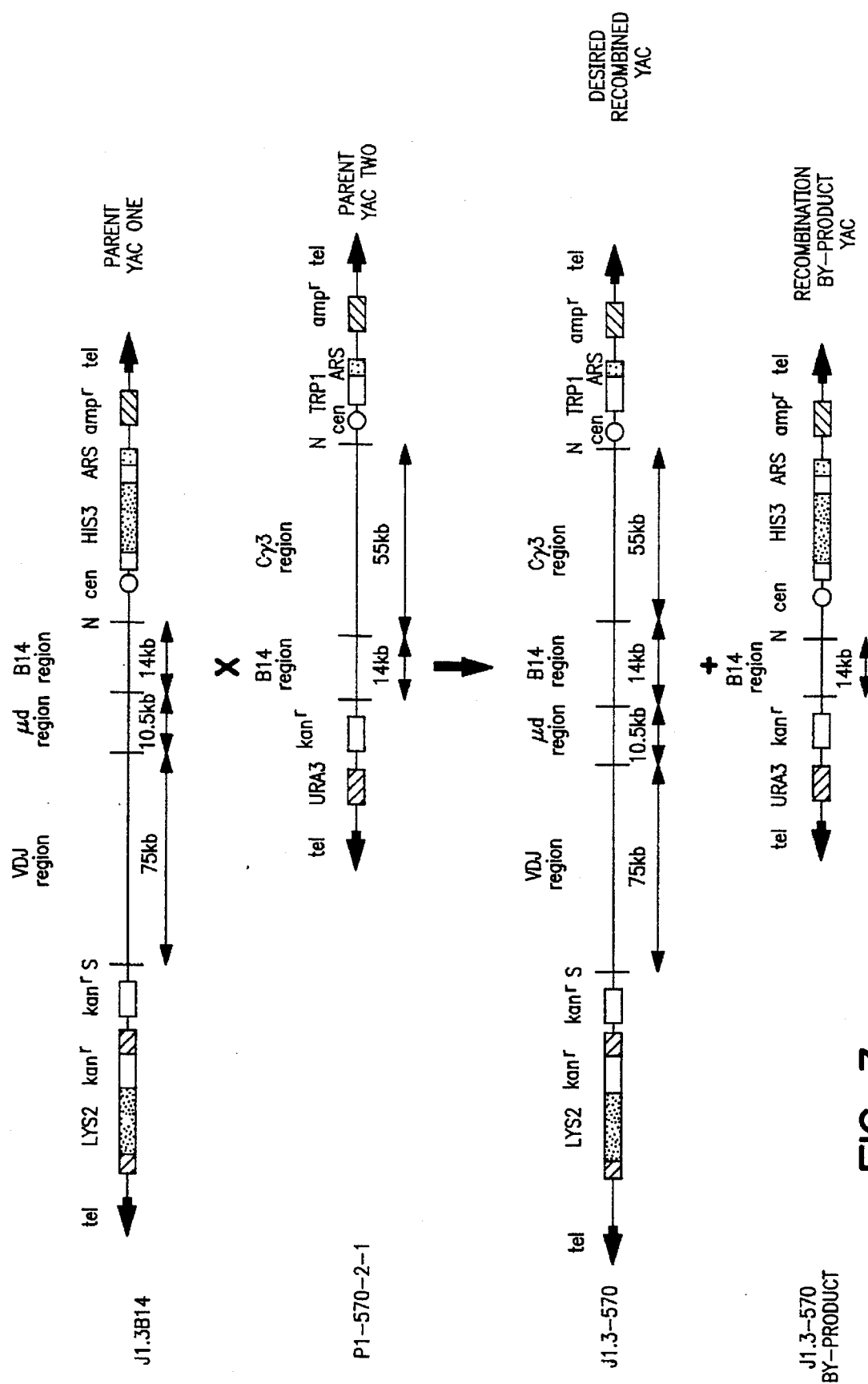
FIG. 3 is a schematic depicting recombination between YAC pairs J1.3-B14 and P1-570-2-1. Partial restriction maps of each input YAC as well as the resulting recombinant YAC products are presented. Recombinant YAC J1.3-570 is an example of a desired recombinant YAC resulting from a multi-step process of the invention wherein a linking YAC, (see NS10-B14, FIG. 2) is used for production of an intermediate YAC (J1.3B14).
Figure 4:
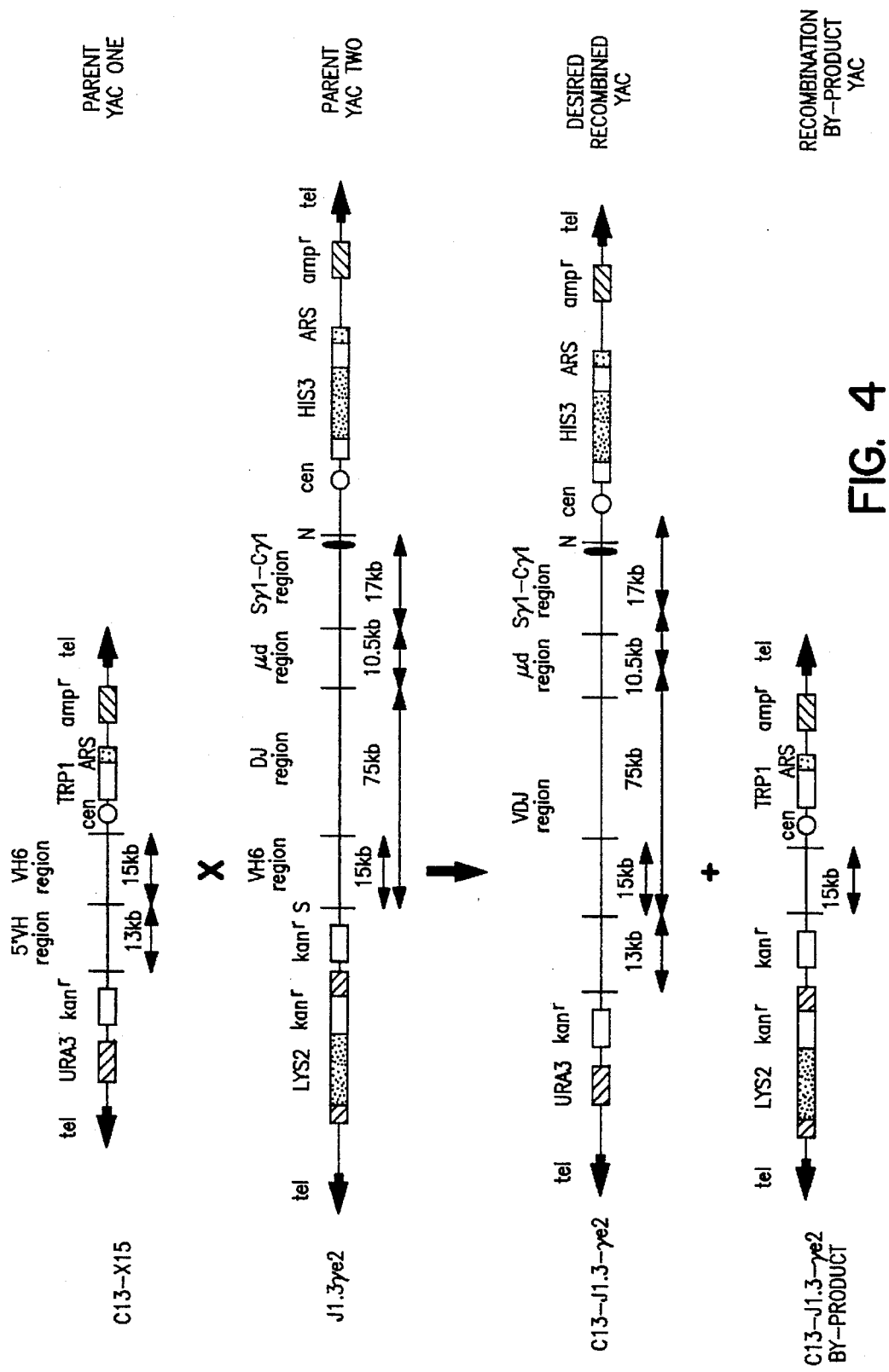
FIG. 4 is a schematic depicting recombination between YAC pairs C13-X15 and J1.3γe2. Partial restriction maps of each input YAC as well as the resulting recombinant YAC products are presented.

Example 1. Construction of Input YACS. In this Example the input YACs used in the recombination experiments of Examples 2 to 11 are provided.

a. Construction of YAC J1.3Lys. FIG. 1 provides a partial restriction map of input YAC J1.3Lys. YAC J3.1LYS (approximately 108 kb) contains as its insert the SpeI-SpeI region of the unrearranged human immunoglobulin heavy chain locus immunoglobulin (H) chain gene (WO 94/00569: hereby incorporated by reference) in pYAC Neo. This fragment contains at least one of each element required for correct rearrangement and expression of a human IgM heavy chain molecule. The fragment contains $V_H6$, the functional diversity (D) segments, all six joining (J) segments, and the Cμ constant region segment (Hofker et al. (1989) *Proc. natl. Acad. Sci.* (*U.S.A.*) 86:5587; Bennan et al. (1988) *EMBO J.* 7:727; Shin et al. (1991) *EMBO J.* 10:3641). To prepare an input YAC having on its arms selectable markers that can be used when inclusion of a genetic selection step is desired, the URA3 "left" arm (in this case the acentromeric arm) of YAC J1.3 (YAC J1.3 was isolated from a YAC library produced in the YAC vector pYACneo[15]; WO 94/00569) was modified to become LYS2$^+$ (and consequently ura3$^-$) by disruption (Rothstein, in *Methods in Enzymology* (1991) 194:281) of the left arm URA3 marker by transforming the yeast strain AB1380 (Mat a, ψ+, ura3, trp1, ade2-1, can1-100, Lys2-1, his5; see Burke et al. (1987) *Science* 236:806–812) that comprises YAC J1.3 with the LYS2/neo fragment from pRV1, a linear fragment containing the LYS2 and neo$^r$ genes flanked by (disrupting) URA3 sequences (Srivastava and Schlessinger *Gene* (1991) 103:53–59). Insertion of the disrupting DNA, increased the total length of the approximately 100 kb J1.3 YAC to about 108 kb. Eight LYS$^+$ transformants were screened for both the ura$^-$ phenotype and for mitotic linkage of the LYS$^+$ and TRP$^+$ phenotypes; 3 isolates showing this desired genetic behavior were identified. All 3 showed mitotic stability of the YAC in the haploid (i.e. YAC retention) to be about 70–80%. Mitotic stability was estimated by a mitotic loss assay. A mitotic loss assay (see Current Protocols in Molecular Biology, Chapter 13, Ibid.) can be performed by culturing a yeast strain comprising a YAC in culture media that, preferably, selects for growth of the cells containing the YAC, transferring a portion of the culture to a non-selective, rich medium, typically YPD, containing solid support (e.g., agar plate) in a way that allows clonal colony growth (typically "streaking" for single colonies) of preferably at least about 20 single, well-separated colonies, more preferably at least about 50 colonies, conveniently after about two days of incubation at about 30° C. Subsequently, each colony is analyzed for the presence or absence of YAC. The analysis is conveniently performed by replica-plating colonies from the non-selective plate to a solid support containing medium that allows selective growth of cells comprising the YAC (i.e., a "dropout" medium plate). After an incubation period to allow for cell growth, typically 1 to 2 days at 30° C., the number of colonies growing on the selective ("dropout") plate is determined and divided by the total number of colonies on the master non-selective plate that were transferred via replica-plating to obtain a value reflecting the "% stability" of the YAC in the strain under the initial growth conditions, i.e., an approximate percentage of the cells in the culture that retained the YAC. Mitotic loss assays used to estimate plasmid mitotic stability are suitable for use herein.

b. Construction of a parental haploid strain bearing YAC J1.3-LYS. Since one of the embodiments of the genetic selection step exemplified in the Examples herein (see below) was designed to require a haploid strain having a his3$^-$ genotype, whereas strain AB1380 is HIS3$^+$ and his5$^-$ the J1.3LYS YAC was transferred into the desired genetic background by mating and sporulation using standard protocols. One of the transformant isolates (J1.3L.6) bearing J1.3LYS YAC was mated to yeast haploid strain YPH857 (Matα, ψ-, ura3-52, trp1-A63, Lys2-801am, ade2-101, his3-Δ200, leu2-Δ1, cyh$^R$). After sporulation of the diploid, tetrad dissection yielded 2 spore clones out of 98 total spores that had retained J1.3LYS, were of the correct mating type, and had the desired his3- and HIS5$^+$ alleles. These two clones were designated J1.3L6.13D and J1.3L6.18C (herein referred to as "13D" and "18C", respectively).

c. Construction of YAC YNNδγ-HIS. FIG. 1 provides a partial restriction map of YAC YNNδγ-HIS. YAC YNNδγ-HIS (approximately 44 kb) contains as its insert a 10.5 kb (Nde-Spe fragment) region of overlap with the 3' terminus of the insert of J1.3LYS (i.e. the Cμ constant region segment) adjoined to an approximately 18 kb region containing the Cγ1 region and the rat heavy chain 3' enhancer derived from pγe2 of Taylor et al. (1992) NAR 20:6287, which is incorporated by reference (see also Lonberg et al. (1994) *Nature* 368:856–859, which is hereby incorporated by reference). YAC YNNδγ-HIS was constructed by isolating the 28.5 kb fragment containing the 10.5 kb Nde-Spe fragment and the 18 kb Cγ1/rat enhancer from plasmid yδγ3, then cloning the 28.5 kb fragment into the not site of pYNN followed by transformation into yeast strain YPH857. pYNN is pYACneo as described by Traver et al. *Proc. Natl. Acad. Sci.* (1989) 86:5898 with the EcoRI cloning site replaced by a NotI cloning site. Yδγ3 was constructed as follows: the 10.5 kb NdeI-SpeI fragment from pJ1NA (described in Choi et al, *Nature Genetics* vol 4 p117 (1993)) was end-filled with Klenow DNA polymerase and SalI linkers (New England Biolabs Inc., Beverly, Mass.) were added. After SalI digestion, the fragment was ligated into the XhoI site of pγe2. Clones containing SalI fragment in the same transcriptional orientation as the Cγ1 gene of pγe2 were identified, and the joined fragment isolated from pγe2 as an about 30 kb NotI fragment. This fragment was ligated to pYNSN vector arms and transformed into yeast. pYNSN was derived from pYNN by NotI/SpeI double digestion followed by NotI linkering, resulting in a pYNN derivative lacking the 613 bp region between the SpeI site and the NotI site. Eight transformants were picked and screened by a Southern blot of XhoI digests. One transformant (designated y2-4) had the correct insert orientation by XhoI digest. This transformant was subjected to further analysis by Southern blots (using pBR or the γ1 region as probes) of both undigested DNA on a CHEF gel, and of restriction-cut DNA (XhoI, BamHI, EcoRI, SphI) on a conventional gel. In all cases, the sizes of fragments were as expected. To prepare an input YAC having on its arms selectable markers that can be used when inclusion of a genetic selection step is desired, and in particular one that is compatible in combination with YAC J1.3LYS, the TRP1 "right" arm (in this case the centromeric arm) marker of YAC y2-4 was modified to become HIS3+ (and consequently trp1⁻) by disruption of the right arm TRP1 marker by transforming the YAC y2-4 host strain with a linear fragment containing a HIS3 gene flanked by the TPR1 gene as follows: plasmid p17H1D was first produced by inserting the *Saccharomyces cerevisiae* yeast HIS3 gene (1.7 kb BamHI fragment with adaptors). (The 1.7 kb BamHI fragment containing HIS3 was isolated from pYACneo (Traver et al, PNAS 86:5898). pYRP17 is from New England Biolabs) into the XbaI site in the TRP1 gene of plasmid YRP17. A 3.1 kb ScaI-StuI fragment from p17H1D containing pBR amp sequences, all TRP1 sequences 5' of the Xba site, the entire HIS3 gene, and 657 bp of TRP1 sequences 3' of the XbaI site, but not including an intact ARS element, was gel purified. YAC y2-4 shares homology to all sequences in this purified fragment, except for the HIS3 sequences. The yeast strain containing y2-4 was then transformed with the ScaI-StuI fragment, and subsequently HIS⁺ transformants were selected and then screened for the trp⁻ phenotype and for linkage (by mitotic loss assays) of the HIS⁺ and URA⁺ phenotypes. Three genetically correct transformants were identified (y3-9, yA-1 and yA-2) and subjected to the same Southern blot analyses as described above for YAC y2-4, which confirmed that these HIS⁺ YAC derivatives had the desired structure. Mitotic stability of YAC integrity was demonstrated by growth of the YAC strain under selection followed by structural analysis. YAC retention (determined by mitotic loss assays) was approximately 50% for the YNNδγ-HIS YAC and 70% for the J1.3Lys YAC.

d. Construction of YAC NS10-B14. FIG. 2 provides a partial restriction map of YAC NS10-B14. YAC NS10-B14 contains as its insert the same 10.5 kb NdeI-SpeI 3' terminal fragment of J1.3LYS (i.e. the Cμ constant region segment) adjoined to an approximately 14 kb BamHI fragment derived from the 5' end of the insert of P1-570 YAC. P1-570 contains P1-570 is a P1 clone from Genome Systems, identified in a screen for human Cγ sequences. To prepare an input YAC having on its arms selectable markers that can be used when inclusion of a genetic selection step is desired, and in particular one that is compatible in combination with YAC J1.3LYS, the TRP1 "right" arm (in this case the centromeric arm) marker of YAC NS10-B14 was modified to become HIS3+ (and consequently trp1⁻) by gene disruption as performed in Example 1c. Mitotic stability of YAC integrity was demonstrated by growth of the YAC strain under selection followed by structural analysis. YAC retention (determined by mitotic loss assays) was approximately 85% for the NS10-B14 YAC.

e. Construction of YAC P1-570-2-1. FIG. 3 provides a partial restriction map of YAC P1-570-2-1. YAC P1-570-2-1 was derived from the P1 clone P1-570 as follows. The 85 kb SalI-NotI insert fragment from P1-570 was isolated, and cloned as a YAC using the BamHI-NotI centric arm and a SalI-BamHI fragment of the acentric arm. During the yeast transformation, a deletion of about 26 kb from the Cγ1 region of the insert had occurred, resulting in a YAC of about 70 kb. The 5' end of the insert (containing the 14 kb BamHI fragment of NS10-B14) was oriented adjacent to the acentric YAC arm. This YAC, P1-570-2-1, which contains the Cγ3 region, is then modified to contain a mouse 3' enhancer obtained as a 15 kb fragment from a mouse genomic phage library (Clontech).

f. Construction of YAC C13-X15. FIG. 4 provides a partial restriction map of YAC C13-X15. YAC C13-X15 contains as the 3' (and overlapping) portion of its insert the approximately 15 kb region of J1.3LYS that contains the $V_{H6}$ region (Choi et al., *Nat. Genet.* 4, 117 (1993) which is hereby incorporated by reference) adjoined to a 13 kb terminal fragment from YAC13.3. YAC13.3 was isolated from the ICRF YAC library (Latin et al., *Proc. Natl. Acad. Sci*, 88:4123–4127 (1991)) using a mixed probe for human immunoglobulin heavy chain VH3 sequences as probe. The mixed probe was produced by PCR using the following oligos as specified for VH3 genes by Campbell et al., *Molecular Immunology* vol 29:193–203 (1992):

VH3-1dr: 5'-CCATGGAGTTTGGGCTGAGC-3' [SEQ ID NO: 5]

VHFR3-COM: 5'-CAGTAATACACGGCCGTGTC -3' [SEQ ID NO: 6]

To prepare an input YAC having on its arms selectable markers that can be used when inclusion of a genetic selection step is desired, and in particular one that is compatible in combination with YAC J1.3LYS, the TRP1 "right" arm (in this case the centromeric arm) marker of YAC C13-X15 was modified to become HIS3+ (and consequently trp1⁻) by gene disruption as performed in Example 1c. Mitotic stability of YAC integrity was demonstrated by growth of the YAC strain under selection followed by structural analysis. YAC retention (determined by mitotic loss assays) was approximately 100% for the C13-X15 YAC, suggesting that multiple copies of the C13-X15 YAC were present in each haploid yeast cell.

Example 2. Meiotic Recombination Between YAC J1.3Lys and YAC YNNδγ-HIS.

a. FIG. 1 provides a schematic depicting the recombination event between YAC J1.3Lys and YAC YNNδγ-HIS and the expected recombinant YAC products. The desired YAC in this particular case is the larger recombinant product YAC (approximately 125 kb) designated YAC J1.3-γe2. By this recombination event heavy constant chain γ1 sequences have been added to the cloned SpeI-SpeI of unrearranged human immunoglobulin heavy chain locus immunoglobulin (H) chain gene to create a more complete heavy chain mini-locus. As will be demonstrated in the following examples, the methods of the present invention enabled additional regions of the gene locus to be assembled in the order found naturally occurring on the chromosome. In addition, as will be seen, genomic regions were juxtaposed (in a functional manner) despite the lack of a YAC clone containing a particular intervening region of overlap by recombination using genetically engineered "linking" YACs.

b. Mating and Sporulation Protocol. Haploid parents were grown under conditions selecting for and maintaining the input YAC. For the mass mating, cells (~5×10$^7$) from each parent culture were mixed, pelleted, washed, and supernatant was decanted. Cells were resuspended in a minimal volume of liquid YPD (or more simply the residual water after decanting) and the cell slurry was spotted to a YPD plate (non-selective for the expected diploid). Incubation was performed at 30° C. for 4–5 hrs, after which cells were spread across the entire plate and incubated at room temperature 20°–25° C. for about 18–24 hrs. Cells were scraped into sterile water and counted. About 10$^8$ cells were pelleted, resuspended in 10 mls of liquid sporulation medium, and incubated at 30° C. for 4–5 days with occasional monitoring for efficient sporulation. Sporulation techniques (including sporulation, spore enrichment, spore isolation, etc) are all described in Guthrie and Find, eds. *Methods in Enzymology* v194:94–109, 146–149. Spores were isolated (Rockmill et al. (1991) in *Methods in Enzymology* 194:147–149 (which is hereby incorporated by reference) and the spore-enriched population was plated to media selective for the desired recombinant YAC (for markers LYS2 and HIS3 on the arms of the desired YAC in this example) and counter-selective for the undesired recombinant YAC and one of the parental YACs, YNNδγ HIS (against URA3 in this example). Colonies arising on the selective media were screened by genetic and by physical methods for the presence of the desired recombinant YAC.

c. Screening and Characterizing YACs. Since the molecular characterization of the candidate YAC clones require preparation of agarose containing large molecular weight DNA blocks of each clone (D. T. Burke, G. F. Carle and M. V. Olsen *Science* 244:1348 (1987)), a high-throughput procedure for generation of small numbers of blocks from multiple strains was developed. Briefly, approximately 10 mls of each culture was grown to late log or early stationary phase, and the cells were pelleted at 1000g for 10 minutes. After decanting off the medium, the pellets were resuspended in the residual medium (approximately 10$^9$ cells in 300 μl). Approximately 150 μl of a 2% low melting point agarose solution in 50 mM EDTA was quickly added, and a single large well of the Bio-Rad well molds were filled with the mixture (Bio-Rad Laboratories, Hercules, Calif.) The blocks were transferred to a 6-well tissue culture plate, each well containing 5 mls of a 4 mg/ml solution of novozyme 234 (Novo Nordisk) in 1M Sorbitol, 50 mM KPi, 100 mM EDTA, pH 5.5. After a 60 minute incubation at 37° C., the novozyme solution was removed by aspiration and the blocks were washed in 100 mM EDTA, 1% Li-dodecyl-sulfate, 1% sarkosyl at 37° C. for 40 minutes. The LiDS-sarkosyl wash repeated twice using fresh LiDS-sarkosyl each time. The blocks were then washed once in 50 mM EDTA, and loaded onto pulsed field gels. After CHEF PFGE (Bio-Rad), the gels were EtBr stained with ethidium bromide, UV nicked, NaOH denatured, and transferred in 0.5M NaOH 1.5M NaCl for 2 hours by capillary transfer onto Hybond N+ positively charged nylon membrane. The blots were hybridized from 1 hour to overnight in hybridization solution containing 10% dextran sulfate and labelled probe. After hybridization, blots were washed, and exposed to autoradiographic film from 10 minutes to 1 hour. Using this streamlined protocol, one person could screen 100–200 candidate YAC clones at a time over a period of two or three days. This rate is at least a 10-fold increase in sample throughput over previously described procedures. Results of the recombination are presented in Table 1 below.

Example 3. Meiotic Recombination between YAC J1.3Lys and YAC NS10-B14. FIG. 2 provides a schematic depicting the recombination event between YAC J1.3Lys and YAC NS10-B14 and the expected recombinant YAC products. The desired YAC in this particular case is the larger recombinant product YAC (approximately 122 kb) designated YAC J1.3-B14. The mating, sporulating, and genetic selection procedures were as described in Example 2. The difference between the recombinations described in Example 2 and Example 3 is that the region being added (i.e., the downstream end of the smaller YAC) is different. In Examples 2 and 3, the upstream YAC is J1.3LYS. In Examples 2 and 3, the region of overlap is the 10.5 kb N-S fragment. In Example 2, the desired recombinant YAC has the 17 kb Cγ1 region of pγe2 added to the 3' end of J1.3LYS, whereas in example 3, the desired recombinant has the 14 kb BamHI fragment derived from P1-570 added to the 3' end of J1.3LYS. Results of the recombination are presented in Table 1 below.

Example 4. Meitoic Recombination between YAC J1.3-B14 and YAC P1-570-2-1. FIG. 3 provides a schematic depicting the recombination event between YAC J1.3-B14 clone #3 and YAC P1-570-2-1 and the expected recombinant YAC products. The desired YAC in this particular case is the larger recombinant product YAC designated YAC J1.3-570. The mating, sporulating and genetic selection steps were performed as described in Example 2, except that selection conditions for the Lys 2 and Trp 1 selectable markers on the desired recombinant YAC were imposed (rather than for Lys 2 and His 3). Selection against Ura 3 was also performed. Results of the recombination are presented in Table 1 below.

Example 5. Meiotic Recombination between YAC C13-X15 and YAC J1.3-γe2. FIG. 4 provides a schematic depicting the recombination event between YAC C13-X15 and YAC J1.3-γe2, and the expected recombinant YAC products. The mating, sporulation and selection were performed as described in Example 2, except that selection was for URA3 and HIS3 and against LYS2. Recombination frequency (presented in Table 1) over the 15 kb region of homology was significantly lower (approximately 500-fold) than expected, and approximately 20-fold lower than the recombination frequencies seen in experiments given in Examples 2, 3, and 4.

Figure 5:
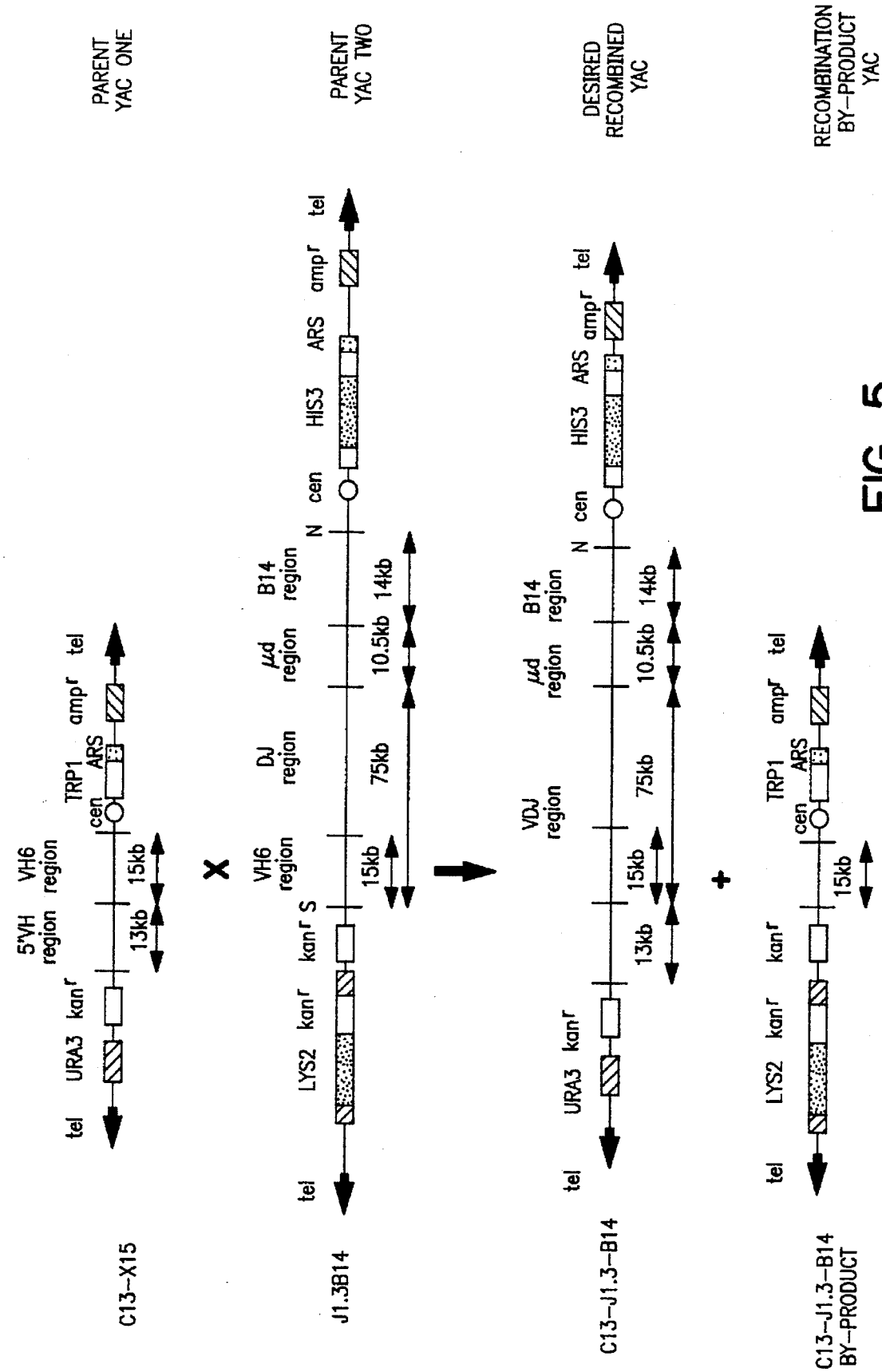
FIG. 5 is a schematic depicting recombination between YACs C13-X15 and J1.3B14. Partial restriction maps of each input YAC and the resulting YAC products are presented.
Figure 6:
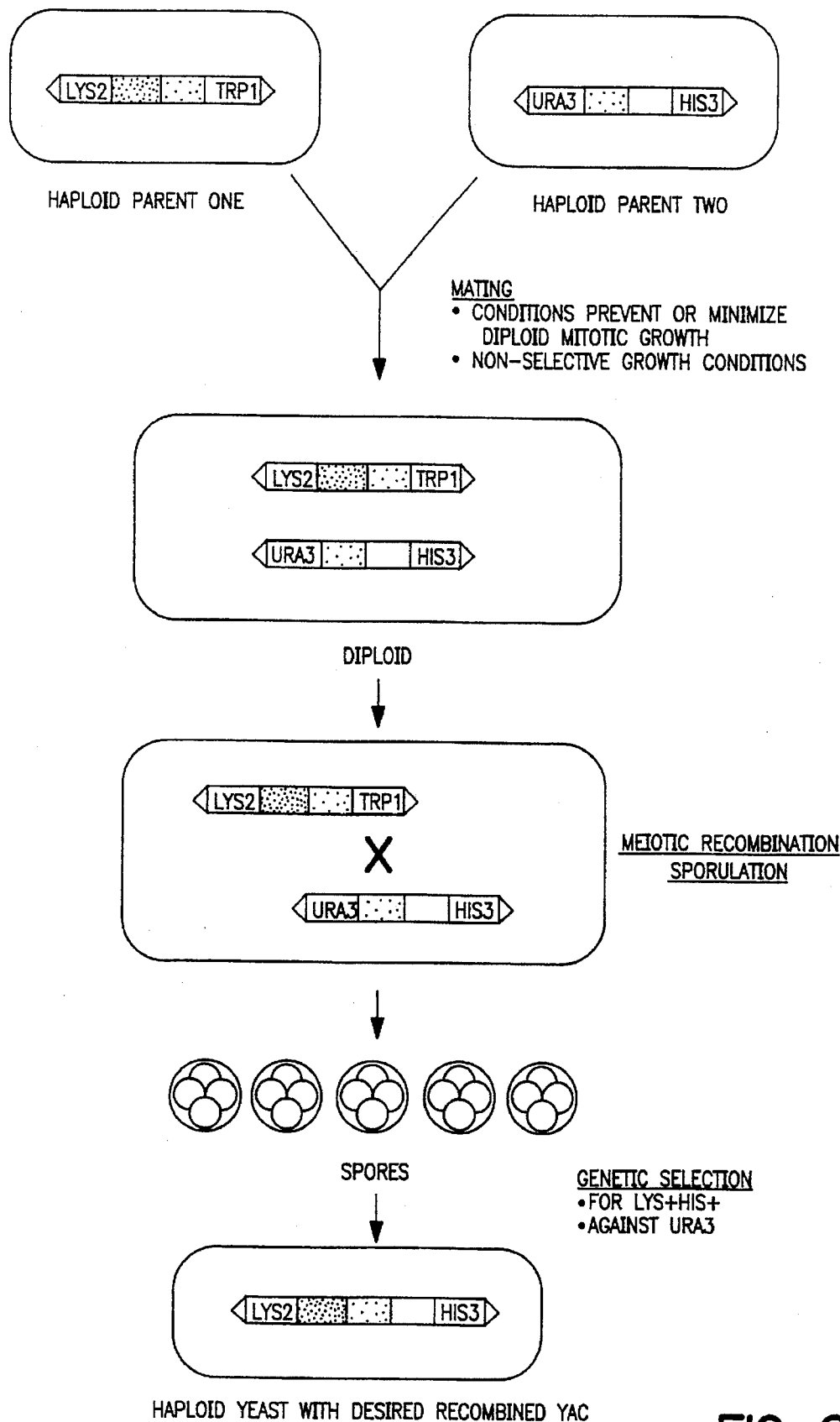
FIG. 6 is a schematic depicting a protocol for recombination of YACs with short regions of homology. The small and large rounded-corner rectangles denote haploid and diploid yeast respectively. YAC arms are denoted as clear boxes, with triangles at ends denoting telomeres. The insert homology regions are depicted as grey boxes.

Example 6. Meiotic Recombination between YAC C13-X15 and YAC J1.3-B14. FIG. 5 provides a schematic depicting the recombination event between YAC C13-X15 and YAC J1.3-B14, and the expected recombination products. The mating, sporulation and selection were performed as described in Example 5.

Example 7. Summary of Recombination Experiments. In Table 1 meiotic recombination frequencies for 4 crosses involving YACs showing diploid incompatibility are presented.

TABLE 1

RECOMBINATION RATES

| Cross | # Spores Plated | # Colonies on Selection | # Correct Recombinants | % Recombination | Adjusted % Recombination | Length of Homology, kb | kb/cM |
|---|---|---|---|---|---|---|---|
| 1. J1.3Lys × YNNδγ-HIS | $5.1 \times 10^4$ | 45 | 9 | 0.053 | 0.17 | 10.5 | 63 |
| 2. J1.3Lys × NS10-B14 | $18 \times 10^4$ | 85 | 15 | 0.025 | 0.046 | 10.5 | 227 |
| 3. J1.3-B14 × 570-2-1 | $3.7 \times 10^4$ | 25 | 9 | 0.072 | 0.099 | 14.5 | 141 |
| 4. J1.3γe2 × C13-X15 | $1.2 \times 10^6$ | 30 | 14 | 0.0035 | 0.010 | 15 | 1500 |

The total number of correct recombinants (identified as such by showing correct behavior of genetic markers, correct size on a pulsed-field gel electrophoresis and containing expected sequences by Southern blotting) was divided by the total number of spores plated and then multiplied by 3 (the average number of viable spores per tetrad) to give the "% recombination". An "adjusted % recombination" was then calculated as detailed below. The average meiotic recombination frequency for yeast genomic DNA has been reported as approximately 3 kb/cM. Suprisingly however, meiotic recombination over short homologies between YACs with short regions of homology was found to be 20–500 fold lower (See Table 1) than that reported for recombination between larger regions of homology. Despite this unexpectedly low recombination frequency, the methods of the present invention provide the means to overcome this biological limitation as demonstrated herein to readily obtain desired recombinant YACs by homologous recombination over relatively short homology regions. Factors such as proximity of centromeres and telomeres, and specific sequence elements such as recombination hotspots may affect recombination frequency.

YAC retention (determined by mitotic loss assays) was approximately 50% for the δγ YAC, 85% for the NS10-B14 YAC and 70% for the J1.3Lys YAC. When each haploid culture was examined on a pulsed-field gel electrophoresis, it appeared that approximately 100% of the δγ and NS10-B14 YACs were "intact" (i.e., of the correct size); whereas approximately 90% of the J1.3Lys YAC was "intact" by the same criteria. Therefore, of the diploids formed during the mass mating in cross 1, only 32 %, on average, had both intact YACs; while in cross 2 this number increases to 54%. These figures were used to derive the "adjusted % recombination" in the table above. The length of overlapping homologous sequences between the two YACs was 10.5 kb in crosses 1 and 2 and 14 kb in cross 3. The data given in Table 1 is for spores purified from the mass-mated cultures by the method of Rockmill et al., (1991) in Guthrie and Fink (eds.) *Methods in Enzymology* 194:147–149. Spore purification was close to 100% in both crosses.

In sharp contrast to the results provided by the methods of the invention described herein, in recombination experiments between YNNδγ-HIS and J1.3LYS (clone 13D) wherein diploid cells were selected (over haploids) by plating to selective media followed by plating to media (ura dropout, trp dropout) selective for each YAC prior to sporulation, wherein diploids were extensively grown, it was found that spores surviving plating on media selective for the desired recombinant (his dropout, lys dropout, and FOA containing did not contain the desired recombinant. It was surprisingly found that the mitotically-grown diploid culture had apparently lost completely the YNNδγ-HIS YAC before undergoing meiosis despite the selection conditions. Accordingly, the methods of the invention provide means to produce and isolate desired recombinant YACs despite diploid incompatibility between input YACs and despite relatively small regions of homology.

Figure 7:
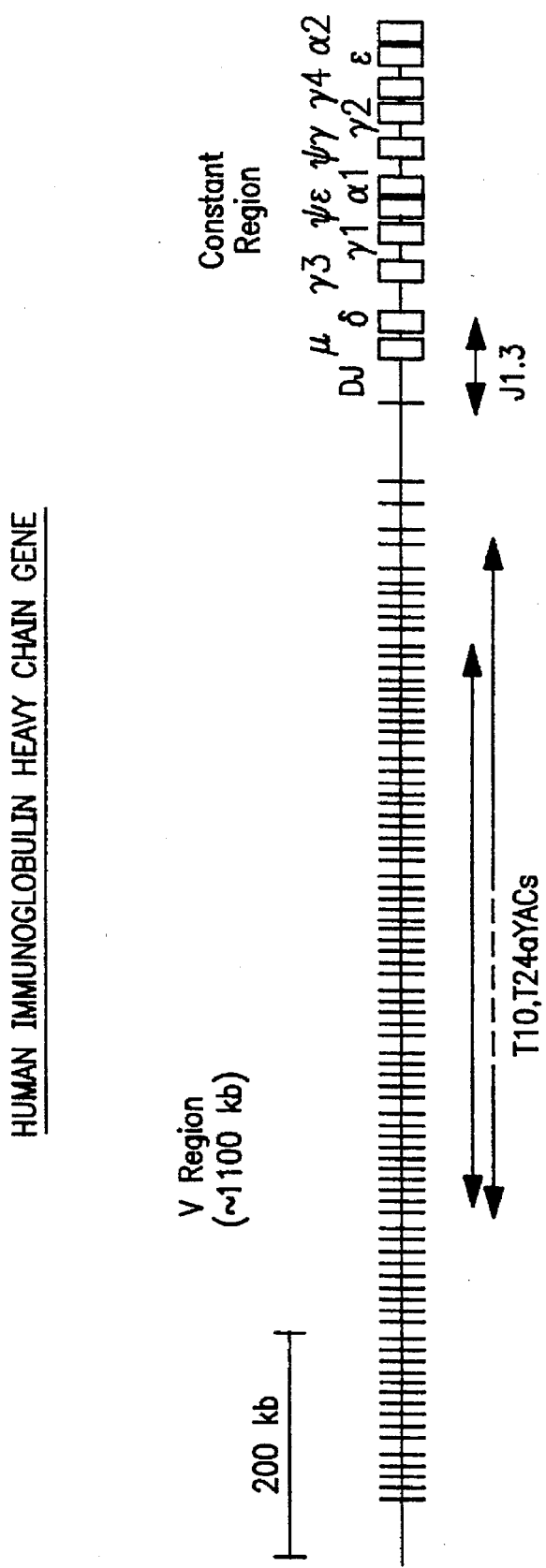
FIG. 7 is a map of the human immunoglobulin heavy chain variable region. The placement of the YACs with respect to the variable gene scale is approximate.
Figure 8:
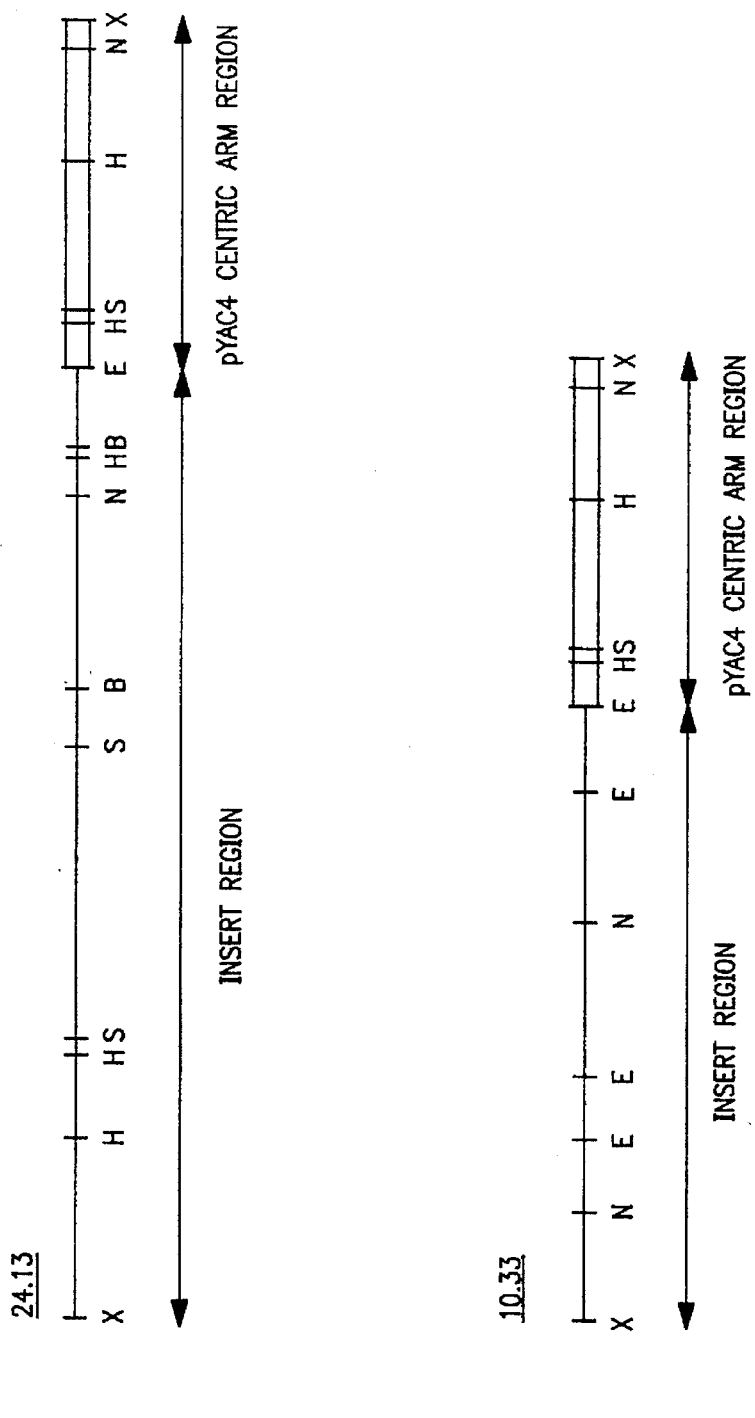
FIG. 8 depicts partial restriction maps of plasmids 24.13 and 10.33. Plasmids are depicted after linearization with XhoI.

Example 8: Analysis of large fragments of the human immunoglobulin heavy chain gene cloned in YACs. Two YACs containing large fragments of the human immunoglobin heavy chain variable region were licensed from the Medical Research Council, UK (see FIG. 7, attached). These YACs (T24a.1 and T10.1) together represent over 50% of the variable gene segments. As depicted in FIG. 8, T24a.1 is a 460 kb YAC containing an intact genomic fragment encompassing at least VH3-26 through VH3-57, and T10.1 is a 370 kb YAC which spans at least VH3-15 through VH3-57, but may carry an uncharacterized deletion of approximately 150 kb. Southern blotting with a centromeric arm specific probe (the 2.7 kb BamHI-PvuII fragment of pBR322) indicated a 17 kb and a 13 kb XhoI terminal fragment for T24a.1 and T10.1 respectively. Since the centric YAC arm contains a bacterial origin and a β-lactamase gene, the terminal portion of the YAC insert adjacent to the centric arm can be cloned by vector arm circularization (Nelson and Brownstein, eds. YAC Libraries, A Users Guide, WH Freeman and Co., pp 3–4, (1994)). These fragments were cloned by ligation of a XhoI digest of total yeast DNA, electroporation of XL1/blue cells (Stratagene), and selection on LB+100 µg/ml plates. The restriction maps of endclones 24.13 and 10.33 from YACs T24a.1 and T10.1 respectively are given in FIG. 9B. These fragments will be used to construct linking YACs which will bridge T24a.1 and T10.1 with J1.3-δγ3 and J1.3-B14.

Example 9: Construction of T24-X15 linking YAC. The 12 kb XhoI-EcoRI fragment from 24.13 is isolated and subcloned into the SalI-EcoRI sites of pGP2b to create pGT10. The 15 kb XhoI fragment from pJ1XK.31 is isolated and cloned into the XhoI site of pGT10 to create pGT10-X15. A clone containing the 5' end of the 15 kb XhoI fragment adjacent to the 12 kb T24 fragment is identified by restriction mapping. The 27 kb NotI fragment from pGT10-X15 is isolated and ligated to pYNN YAC vector arms and transformed into a yeast host strain such as YPH857 (Yeast Genetics Stock Center, Berkeley Calif.) or AB1380 (Washington University). Those YACs containing the T24 fragment adjacent to the acentric YAC arm can be identified by restriction digest Southern analysis, designated T24-X15 linking YAC, and recombined with J1.3-δγ3 and J1.3-B14 according to the invention to yield YAC T24-J1.3δγ3 and YAC T24-J1.3-B14. Recombinants can be selected for URA3 and HIS3 and against LYS2 on media lacking uracil and histidine and containing 0.2% alpha-amino-adipate (Chatoo et al., *Genetics* 93:51 (1979)).

Example 10: Recombination of T24a.1 to YAC T24-J1.3δγ3 and YAC T24-J1.3-B14.

LYS2 derivatives of T24a.1 and T10.1 can be obtained by transformation of T24a.1 and T10.1 yeast host strains with the 10 kb HindIII fragment from pRV1, followed by selection for lysine prototrophy. Clones containing the LYS2 pRV1 fragment targeted into the acentric arm of the T24a.1 and T10.1 YACs can be identified by PFGE Southern blotting using a LYS2 specific probe. The resultant YAC, T24L recombined to YAC T24-J1.3δγ3 and YAC T24-J1.3-B14 by selecting for LYS2 and HIS3 and against URA3 on media lacking lysine and histidine and containing FOA. YAC T10.1 is similarly recombined to YAC T10-J13Sγ3 and YAC T10-J13-B14.

Example 11: Construction of linking YACs by LR-PCR.

In some cases, the terminal fragments of YACs necessary to construct linking YACs will not be readily clonable by vector circularization. A number of alternative methods have been described (summarized in Nelson and Brownstein, eds. YAC Libraries, A Users Guide, W. H. Freeman and Co., pp 102–107, (1994)) but these approaches produce clones of generally less than 3 kb. Although using the methods of the present invention yeast recombination is possible over such short tracts, it would be more preferred to have overlapping regions of about 10 kb. Further, the assembly of terminal fragments into a linking YAC requires several ligation and transformation steps in *E. coli* and in yeast. In other cases, convenient restriction sites may not be available for the isolation of the terminal fragment from the vector arm portion of the vector circularization plasmid. For example, there are multiple EcoRI sites within the 8.5 kb terminal fragment of the T10.1 endclone 10.33, precluding isolation of the entire insert as a XhoI-EcoRI fragment.

The terminal fragments of 10.33 and 24.13 were isolated by long range PCR (LR-PCR; Perkin Elmer Corporation, Norwark, Conn.) using the XL-PCR kit (Perkin Elmer). The following oligos, specific for YAC centric vector arm sequences, were used to amplify the inserts:

LRVT-1F: 5'-CTC TCG AGG GCT TGG TTA TGC CGG TAC T-3' [SEQ ID NO: 7] and

LRVT-1R: 5'-CTC TCG AGC CTC TGA CTT GAG CGT CGA T-3' [SEQ ID NO: 8].

Bands of about 8.5 kb and 12 kb were amplified from 10.33 and 24.13 respectively, and isolated as XhoI fragments of about 8.5 kb and 12 kb for subsequent cloning steps.

The linking YAC can be partially constructed by LR-PCR. As depicted in FIG. 9A and FIG. 9B, a set of 4 oligos were synthesized and used to amplify the 10.33 and 24.13 insert fragments and the J1XK.31 insert fragment. The primer sequences were:

S1AR: 5'-AAG CGG CCG CAT GAA TTC TAT CTG GGA AGT GAA TGG AGA C-3' [SEQ ID NO: 1];

S3'CX: 5'-TAG CGG CCG CAT TAG AAT TCA GCT GCA TGT GTC AGA GGT T-3' [SEQ ID NO: 2];

S2'AX1: 5'-ATT ACC CTG TTA TCC CTA GGC CGA ACA GGC AGA CAT CTG TGA-3' [SEQ ID NO: 3];

S2CR1: 5'-GGC CTA GGG ATA ACA GGG TAA TAC TCT CGG TAG CCA AGT TGG-3' [SEQ IS NO: 4].

NotI sites were included in S1 and S3', and i-SceI sites were included in S2 and S2'. The J1XK.31 derived amplification product is joined to the 10.33 or the 24.13 amplification products by digestion of both products with i-SceI, ligated to form circles, and digested with NotI to form linearized, joined fragments. These NotI fragments are cloned in pYNN vector arms, transformed into yeast, and analyzed for structure by restriction digest Southern analysis.

All publications and patent applications mentioned in this specification are herein incorporated by reference to the same extent as if each individual publication or patent application was specifically and individually indicated to be incorporated by reference. The references discussed herein are provided solely for their disclosure prior to the filing date of the present application. Nothing herein is to be construed as an admission that the inventors are not entitled to antedate such disclosure by virtue of prior invention.

The invention now being fully described, it will be apparent to one of ordinary skill in the art that many changes and modifications can be made thereto without departing from the spirit or scope of the appended claims.

---

What is claimed is:

1. A method of producing a recombinant YAC, comprising the steps of
   (a) mating a first haploid yeast cell comprising a first YAC to a second haploid yeast cell comprising a second YAC having a homology region with the first YAC, to obtain a diploid yeast cell, said first and second YACs being maintained without rearrangements prior to meiotic recombination by limiting mitotic doubling of the diploid to less than or equal to 8 doublings,
   (b) sporulating the diploid and/or its mitotic progeny, to obtain spores, and then
   (c) identifying spores that comprise the recombinant YAC.

2. The method of claim 1, wherein step (a) comprises a mass mating between cultures of the first and second haploid yeast cells.

3. The method of claim 1, wherein in step (a) mating occurs in the absence of a selection for the diploid comprising both the first and second YACs.

4. The method of claim 1, wherein diploid mitotic doubling in step (a) is less than or equal to 3 doublings.

5. The method of claim 2, wherein in step (a) the mating step is less than or equal to 5 diploid-doubling times.

6. The method of claim 5, wherein the mating step is less than or equal to 3 diploid-doubling times.

7. The method of claim 3, wherein step (c) comprises identifying spores that comprise the recombinant YAC by culturing spores under conditions that select for growth of spores comprising the recombinant YAC, and optionally, selecting against spores comprising an undesired recombinant YAC and further optionally selecting against spores or cells comprising one or both unrecombined first and second YACs.

8. The method of claim 7, wherein in step (c) selecting for growth of spores comprising the recombinant YAC comprises selecting for at least one selectable marker present on the recombinant YAC.

9. The method of claim 8, wherein selecting for growth of spores comprises selecting for at least two selectable markers that are present on the recombinant YAC but are not present on an undesired recombinant YAC.

10. The method of claim 1, wherein the homology region between the first and second YAC is less than about 40 kilobases.

11. The method of claim 10, wherein the homology region is less than about 20 kilobases.

12. The method of claim 10, wherein the homology region is less than about 5 kilobases.

13. The method of claim 1, wherein said mating step comprises an initial period and a remaining period and during the mating step cells are maintained at a higher temperature during the initial period of the mating step than during the remaining period.

14. The method of claim 13, wherein the temperature during the initial period is about 25° to about 35° C. and the temperature during the remaining period is about 15° to about 25° C.

15. The method of claim 1, further comprising the step of isolating the recombinant YAC.

16. A method of producing a desired recombinant YAC, comprising the steps of
   (a) obtaining a first haploid yeast cell comprising a first input YAC,
   (b) obtaining a second haploid yeast cell comprising a second input YAC,
   (c) obtaining a third haploid yeast cell comprising a linking YAC having a first homology region with the first input YAC and a second homology region with the second input YAC,
   (d) obtaining an intermediate haploid yeast cell comprising an intermediate recombinant YAC by meiotic homologous recombination between the linking YAC and the first input YAC, and
   (e) obtaining a final yeast cell comprising the desired recombinant YAC by meiotic homologous recombination between the intermediate YAC and the second input YAC, wherein steps (a), (b), and (c) are performed in any order wherein the steps (d) and/or (e) comprise the steps of (1) mating the first haploid yeast cell to the third haploid yeast cell in the case of step (d) to obtain a first diploid yeast cell and mating the intermediate haploid yeast cell to the second haploid yeast cell in the case of step (e) to obtain a second diploid yeast cell, said YACs being maintained without rearrangements prior to meiotic recombination by limiting mitotic doubling of the diploid to less than or equal to 8 doublings.

17. The method of claim 16, wherein either the first homology region or the second homology region is less than about 40 kilobases.

18. The method of claim 16, wherein both the first homology region and the second homology region are less than about 40 kilobases.

19. The method of claim 16, wherein the steps (d) and/or (e) comprise the steps of (1) sporulating the first and second diploids and/or their mitotic progeny, to obtain spores, and then (2) identifying spores comprising the intermediate YAC in the case of step (d) and spores comprising the desired recombinant YAC in the case of step (e).

20. The method of claim 16, wherein the linking YAC is constructed by a method comprising the step of (a) obtaining a first vector having the first homology region and a second vector having the second homology region;

(b) amplifying the first homology region and the second homology region by long-range polymerase chain reaction; and (c) ligating said amplified first and second homology regions to each other and to a YAC vector to create said linking YAC.

21. The method of claim 20, wherein the amplification step comprises (a) extending a first primer able to bind to a region upstream of the first homology region, (b) extending a second primer able to bind to a region downstream of the first homology region, (c) extending a third primer able to bind to a region upstream of the second homology region.

(d) extending a fourth primer able to bind to a region downstream of the second homology region, wherein the first and fourth primers each comprise a first restriction enzyme site sequence that is not present in either amplified homology region but is present as a cloning site in a linking YAC vector, and wherein the second and third primers each comprise a second restriction enzyme site sequence that is different from the first restriction enzyme site sequence and that is not present in either amplified homology region nor in the linking YAC vector arms.

22. The method of claim 16, wherein the steps (d) and/or (e) comprise the steps of (1) sporulating the first and second diploids and/or their mitotic progeny, to obtain spores, and then (2) identifying spores comprising the intermediate YAC in the case of step (d) and spores comprising the desired recombinant YAC in the case of step (e) by culturing spores by selecting for growth of spores or cells comprising the intermediate or desired recombinant YAC, and optionally, selecting against spores comprising an undesired recombinant YAC and further optionally selecting against spores or cells comprising one or both unrecombined first input and linking YACs in the case of step (d) or intermediate and second input YACs in the case of step (e).

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
    ( A ) LENGTH: 40
    ( B ) TYPE: nucleic acid
    ( C ) STRANDEDNESS: single
    ( D ) TOPOLOGY: linear ( x i ) SEQUENCE DESCRIPTION: SEQ ID NO: 1:

AAGCGGCCGC ATGAATTCTA TCTGGGAAGT GAATGGAGAC    40

( 2 ) INFORMATION FOR SEQ ID NO: 2:

( i ) SEQUENCE CHARACTERISTICS:
    ( A ) LENGTH: 40
    ( B ) TYPE: nucleic acid
    ( C ) STRANDEDNESS: single
    ( D ) TOPOLOGY: linear ( x i ) SEQUENCE DESCRIPTION: SEQ ID NO: 2:

TAGCGGCCGC ATTAGAATTC AGCTGCATGT GTCAGAGGTT    40

( 2 ) INFORMATION FOR SEQ ID NO: 3:

( i ) SEQUENCE CHARACTERISTICS:
    ( A ) LENGTH: 42
    ( B ) TYPE: nucleic acid
    ( C ) STRANDEDNESS: single
    ( D ) TOPOLOGY: linear ( x i ) SEQUENCE DESCRIPTION: SEQ ID NO: 3:

ATTACCCTGT TATCCCTAGG CCGAACAGGC AGACATCTGT GA    42

( 2 ) INFORMATION FOR SEQ ID NO: 4:

( i ) SEQUENCE CHARACTERISTICS:
    ( A ) LENGTH: 42
    ( B ) TYPE: nucleic acid
    ( C ) STRANDEDNESS: single
    ( D ) TOPOLOGY: linear ( x i ) SEQUENCE DESCRIPTION: SEQ ID NO: 4:

GGCCTAGGGA TAACAGGGTA ATACTCTCGG TAGCCAAGTT GG    42

( 2 ) INFORMATION FOR SEQ ID NO: 5:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 5:

CCATGGAGTT TGGGCTGAGC    20

( 2 ) INFORMATION FOR SEQ ID NO: 6:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 6:

CAGTAATACA CGGCCGTGTC 20

( 2 ) INFORMATION FOR SEQ ID NO: 7:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( x i ) SEQUENCE DESCRIPTION: SEQ ID NO: 7:

CTCTCGAGGG CTTGGTTATG CCGGTACT 28

( 2 ) INFORMATION FOR SEQ ID NO: 8:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( x i ) SEQUENCE DESCRIPTION: SEQ ID NO: 8:

CTCTCGAGCC TCTGACTTGA GCGTCGAT 28